（12）United States Patent
Bachalo et al.

(10) Patent No.: US 10,578,538 B2
(45) Date of Patent: Mar. 3, 2020

(54) MULTIPLE BEAM AND CONVERGENT LIGHT ILLUMINATION CROSSED-BEAM IMAGING

(71) Applicant: ARTIUM TECHNOLOGIES, INC., Sunnyvale, CA (US)

(72) Inventors: William D. Bachalo, Los Altos Hills, CA (US); Gregory A. Payne, Richland, WA (US); Khalid Ibrahim, Hatfield, PA (US); Michael J. Fidrich, San Jose, CA (US)

(73) Assignee: ARTIUM TECHNOLOGIES, INC., Sunnyvale, CA (US)

( * ) Notice: Subject to any disclaimer, the term of this patent is extended or adjusted under 35 U.S.C. 154(b) by 0 days.

(21) Appl. No.: 15/552,263

(22) PCT Filed: Feb. 17, 2016

(86) PCT No.: PCT/US2016/018352
§ 371 (c)(1),
(2) Date: Aug. 18, 2017

(87) PCT Pub. No.: WO2016/134076
PCT Pub. Date: Aug. 25, 2016

(65) Prior Publication Data
US 2018/0045634 A1 Feb. 15, 2018

Related U.S. Application Data

(60) Provisional application No. 62/118,962, filed on Feb. 20, 2015.

(51) Int. Cl.
*G01N 15/12* (2006.01)
*G01N 15/02* (2006.01)
(Continued)

(52) U.S. Cl.
CPC ..... *G01N 15/0227* (2013.01); *G01N 15/0205* (2013.01); *G01N 15/0211* (2013.01);
(Continued)

(58) Field of Classification Search
CPC ..... G01N 15/0205–2015/03; G01N 2015/025; G01N 15/0211; G01N 2015/1037; G06T 7/571; G06T 7/593; G06T 7/60
See application file for complete search history.

(56) References Cited

U.S. PATENT DOCUMENTS 6,081,577 A * 6/2000 Webber ............... G01N 23/046
378/23
7,733,485 B2 * 6/2010 Sandler ............. G01N 15/0227
356/335
(Continued)

OTHER PUBLICATIONS

European Patent Office, International Search Report for counterpart International Application No. PCT/US2016/018352, 4 pgs. (dated Jun. 1, 2016).
(Continued)

*Primary Examiner* — Rebecca C Bryant
(74) *Attorney, Agent, or Firm* — Womble Bond Dickinson (US) LLP

(57) ABSTRACT

Methods and apparatuses to image particles are described. A plurality of illuminating light beams propagating on multiple optical paths through a particle field are generated. The plurality of illuminating light beams converge at a measurement volume. A shadow image of a particle passing through a portion of the measurement volume at a focal plane of a digital camera is imaged. Shadow images of other particles in the particle field are removed using the plurality of illuminating light beams.

33 Claims, 19 Drawing Sheets

(51) Int. Cl.
G06T 7/571 (2017.01)
G06T 7/593 (2017.01)
G06T 7/60 (2017.01)
G01N 15/00 (2006.01)

(52) U.S. Cl.
CPC ....... G01N 15/12 (2013.01); G01N 2015/025 (2013.01); G01N 2015/03 (2013.01); G06T 7/571 (2017.01); G06T 7/593 (2017.01); G06T 7/60 (2013.01)

(56) References Cited

U.S. PATENT DOCUMENTS

| | | | |
|---|---|---|---|
| 8,194,170 | B2 | 6/2012 | Golub et al. |
| 8,477,307 | B1* | 7/2013 | Yufa .................... G01N 21/658 356/337 |
| 8,681,251 | B2* | 3/2014 | Kim .................... H04N 5/23245 348/305 |
| 2002/0111546 | A1* | 8/2002 | Cook .................... A61B 5/0059 600/322 |
| 2006/0175561 | A1* | 8/2006 | Estevadeordal ........ G01F 1/704 250/573 |
| 2010/0302396 | A1 | 12/2010 | Golub et al. |
| 2013/0342684 | A1 | 12/2013 | Keranen et al. |

OTHER PUBLICATIONS

European Patent Office, Written Opinion for counterpart International Application No. PCT/US2016/018352, 4 pgs. (dated Jun. 1, 2016).
Wang, Q., "High Speed Stereoscopic Shadowgraph Imaging and its Digital 3D reconstruction," *Measurement Science and Technology*, IOP, vol. 22, No. 6, May 4, 2011, p. 65302—Bristol, Great Britain.
The International Bureau of WIPO—International Preliminary Report on Patentability for International Application No. PCT/US2016/018352 dated Aug. 22, 2017, 6 pgs.
Bachalo, W.D., "Method for Measuring the Size and Velocity of Spheres by Dual-beam Light-Scatter Interferometry," Applied Optics, vol. 19, No. 3, pp. 363-370, Feb. 1, 1980.
Bachalo, W.D. and Houser, M.J., "Phase Doppler Spray Analyzer for Simultaneous Measurements of Drop Size and Velocity Distributions", Optical Engineering, vol. 23, No. 5, Sep.-Oct. 1984.
Bachalo, W.D. and Sankar, S.V., "Phase Doppler Particle Analyzer", CRC handbook of Fluid Dynamics, 1996.
Brenguier J.L., Bourrianne, T., Coelho, A.D., Isbert, J., Peytavi, R., Trevarin, D., and Weschler, P. "Improvements of droplet size distribution measurements with the Fast-FSSP (Forward Scattering Spectrometer Probe)," Journal of Atmospheric and Oceanic Technology, vol. 15, No. 5, pp. 1077-1090, 1998.
Gober, S.G., Isaac, G.A., and Stapp, J.W., "Characterization of Aircraft Iicing Environments that include Supercooled large Drops," Journal of Applied Meteorology, vol. 40, 2001.
Kim, K.S. And Kim, S. S., 1994, "Drop Sizing and Depth-Of-Field Correction in TV Imaging," Atomization and Sprays, No. four, pp. 65-78.

Korolev, A.V., Kuznetsov, S.V., Makarov, Yu E., and Novikov, V.S., "Evaluation of Measurements of Particle Size and Sample Area from Optical Array Probes," Journal of Atmospheric and Oceanic Technology, vol. 8, 1991.
Korolev, A.V., Strapp, J.W., and Isaac, G.A., "Evaluation of the Accuracy of PMS Optical Array Probes," Journal of Atmospheric and oceanic Technology, vol. 15, 1998.
Lebrun, D., Touil, C.E., and Ökzul, C., "Methods for the deconvolution of defocused-image pairs recorded separately on two CCD cameras: application to particle sizing", Applied Optics, vol. 35, Issue 32, pp. 6375-6381, Nov. 10, 1996.
Lee, S.Y. And Kim, Y.D., "Sizing of Spray Particles Using Image Processing," Proc. Symp. !ICLASS, Sorrento, Italy, 2003.
Lecuona, P.A. Sosa, P.A. Rodriguez, and R.I. Zequeira, 2000, " Volumetric Characterization of Dispersed Two-Phase Flows by Digital Image Analysis," Measurement Science and Technology, No. 11, VP 1152 -1161.
Malot, H. And Blaisot, J.B., 2000, "Droplet Size Distribution and Sphericity Measurements of Low-Density Sprays through Image Analysis," Part. Part Syst. Charact., No. 17, pp. 146-158.
Oldenburg, J.R. And Ide, R.F., "Comparison of Two Droplet Sizing Systems in an Icing Wind Tunnel," AIAA-90-0668, 28th Aerospace Sciences Meeting, Reno, Nevada, Jan. 8-11, 1990.
Rudoff, R.C. and Bachalo, W.D, 'Performance of the Phase Doppler Particle Analyzer Icing Cloud Droplet Sizing Probe in the NASA Lewis Icing Research Tunnel, 30th Aerospace Sciences Meeting & Exhibit, Jan. 6-9. 1992.
Rudoff, R.C., Oldenburg, J.R., and Bachalo, W.D., Liquid Water Content Measurement Using the Phase Doppler Particle Analyzer in the NASA Lewis Icing Research Tunnel, 31st Aerospace Sciences Meeting & Exhibit, Jan. 11-14, 1993.
Strapp, J.W., Albers, F., Reuter, A., Korolev, A.V., Maixner, U., Rashke, E., and Vukovic, Z., "Laboratory measurements of the response of a PMS OAP-2DC," Journal of Atmospheric and Oceanic Technology vol. 18, No. 7, pp. 1150-1170, 2001.
Y. Flardalupas et al., "A Shadow Doppler technique for sizing particles of arbitrary shape", 3rd Congress on Optical Particle Sizing, Yokohama, Japan, 1993, 10 pages.
M. Maeda et al., "Accuracy of Particle Flux and Concentration Measurement by Shadow Doppler Velocimetry", (no date), 11 pages.
Hiroshi Morikita et al., "Measurement of Size and Velocity of Arbitrary Shaped Particles by LDA Based Shadow Image Technique", (no date), 8 pages.
Stephan Zimmermann et al., "PSI: An innovative method to determine and to classify particles during the thermal spray process", (no date), 5 pages.
Korolev, et al., "Evaluation of Measurements of Particle Size and Sample Area from Optical Array Probes," Journal of Atmospheric and Oceanic Technology, Aug. 1991, pp. 514-522, vol. 8, American Meteorological Society, 9 pages.
Korolev, et al., "Evaluation of the Accuracy of PMS Optical Array Probes," Journal of Atmospheric and Oceanic Technology, Jun. 1998, 13 pp., vol. 15, No. 3, American Meteorological Society.

* cited by examiner

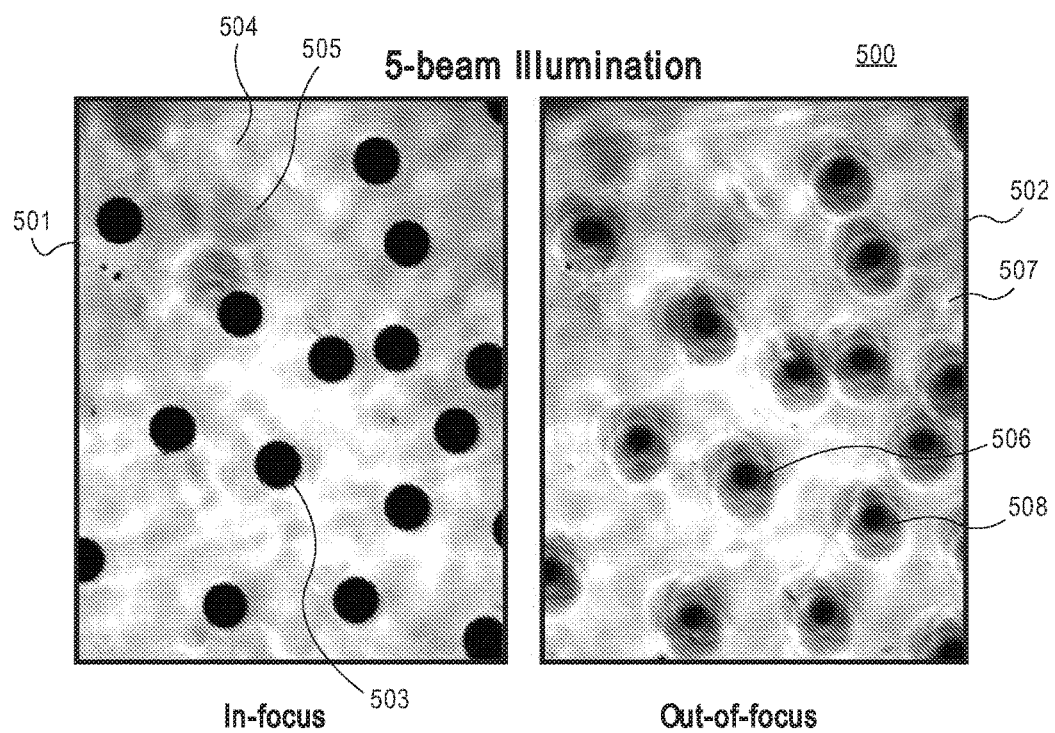
FIG. 5A1
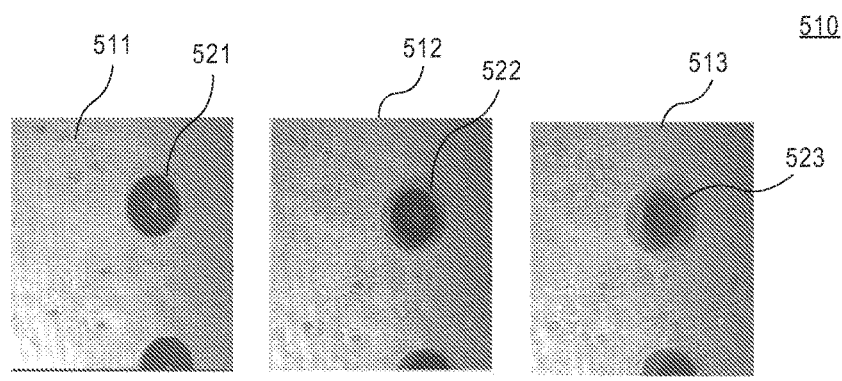
FIG. 5A2

MULTIPLE BEAM AND CONVERGENT LIGHT ILLUMINATION CROSSED-BEAM IMAGING

CROSS-REFERENCE TO RELATED APPLICATIONS

This patent application is a U.S. National Phase application under 35 U.S.C. § 371 of International Application No. PCT/US2016/018352, filed on Feb. 17, 2016, entitled MULTIPLE BEAM AND CONVERGENT LIGHT ILLUMINATION CROSSED-BEAM IMAGING, which claims the benefit of priority from U.S. Provisional Application No. 62/118,962, filed on Feb. 20, 2015.

GOVERNMENT LICENSE RIGHTS

This invention was made with government support under Contract No. NNX14CC65P awarded by National Aeronautics and Space Administration (NASA). The government has certain rights in the invention.

FIELD

Embodiments of the invention relate to particle imaging. More particularly, embodiments of the invention relate to imaging of particles using convergent light.

BACKGROUND

A very wide range of industrial processes use liquid droplets and solid particles of irregular shapes and sizes. Grinding powders, medical inhalers, and spray painting are just a few such examples. Industrial processes including coatings produced by thermal and other sprays typically involve determinations of particle parameters—for example, particle size, shape, velocity, and position in space. The area of aircraft icing involves supercooled water droplets in the presence of ice crystals and ice particles (spherical frozen droplets). Existing techniques cannot accurately and reliably measure the size of these particles. Furthermore, existing techniques cannot separate the liquid droplets from the ice particles and ice crystals.

Existing particle imaging techniques include incorporating bright-field imaging using arc flash lamps, pulsed lasers, and pulsed LEDs for illumination. These techniques typically use charge-coupled device ("CCD") cameras or Complimentary Metal Oxide Semiconductor ("CMOS") cameras to record the shadow images of the particles. These techniques typically use collimated or nearly collimated light with diffusers to illuminate the particle field. In these techniques, however, the out of focus particles under relatively dense particle field conditions typically produce shadows that complicate the detection and measurement of the in focus particle shadow images. In addition, larger particles in the light beam path can extinguish or obscure the light beam which causes a loss of the smaller particle image at the sample volume. Such losses of images result in an unacceptable bias in the sampling statistics.

SUMMARY

Methods and apparatuses to image particles are described. For an embodiment, a plurality of illuminating light beams propagating on multiple optical paths through a particle field are generated. The plurality of illuminating light beams converge at a measurement volume. A shadow image of a particle passing through a portion of the measurement volume at a focal plane of a digital camera is imaged. Shadow images of other particles in the particle field are removed using the plurality of illuminating light beams.

For an embodiment, a plurality of illuminating light beams propagating on multiple optical paths through a particle field are generated. The plurality of illuminating light beams converge at a measurement volume. A shadow image of a particle passing through a portion of the measurement volume at a focal plane of a digital camera is imaged. Shadow images of other particles in the particle field are removed using the plurality of illuminating light beams. The plurality of illuminating light beams may comprise multiple wavelengths.

For an embodiment, a non-transitory machine-readable medium comprises data that when accessed by a data processing system, cause the data processing system to perform a method to image particles that involves generating a plurality of illuminating light beams propagating on multiple optical paths through a particle field, the plurality of illuminating light beams converging at a measurement volume; and imaging a shadow image of a particle present through a portion of the measurement volume at a focal plane of a first digital camera. Shadow images of other particles in the particle field are reduced or removed using the plurality of illuminating light beams.

For an embodiment, a non-transitory machine-readable medium comprises data that when accessed by a data processing system, cause the data processing system to perform a method to image particles that involves generating a plurality of illuminating light beams propagating on multiple optical paths through a particle field, the plurality of illuminating light beams converging at a measurement volume; and imaging a shadow image of a particle present through a portion of the measurement volume at a focal plane of a first digital camera. Shadow images of other particles in the particle field are removed using the plurality of illuminating light beams. The plurality of illuminating light beams comprise multiple wavelengths.

For an embodiment, an apparatus to image particles comprises a transmitter to generate a plurality of illuminating light beams propagating on multiple optical paths through a particle field, the plurality of illuminating light beams converging at a measurement volume. A receiver is coupled to the transmitter. The receiver comprises an imaging optics; and a first digital camera coupled to the imaging optics to provide a shadow image of a particle passing through the measurement volume at a focal plane of the first digital camera. The plurality of illuminating light beams are configured to remove shadow images of other particles in the particle field. A processor is coupled to least one of the transmitter and the receiver.

For an embodiment, an apparatus to image particles comprises a transmitter to generate a plurality of illuminating light beams propagating on multiple optical paths through a particle field, the plurality of illuminating light beams converging at a measurement volume. A receiver is coupled to the transmitter. The receiver comprises an imaging optics; and a first digital camera coupled to the imaging optics to provide a shadow image of a particle passing through the measurement volume at a focal plane of the first digital camera. The plurality of illuminating light beams are configured to remove shadow images of other particles in the particle field. A processor is coupled to least one of the transmitter and the receiver. For an embodiment, the plurality of illuminating light beams comprise multiple wavelengths. For another embodiment, the plurality of illuminating light beams use a single wavelength.

Other features and advantages of embodiments of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements, in which:

FIG. 5A1 is a view showing examples of five-beam illumination images acquired in a relatively dense spray.

FIG. 5A2 is a view showing examples of multi-beam illumination images of particles that pass the measurement volume at different distances from the focal plane of the imaging system.

DETAILED DESCRIPTION

Methods and apparatuses to image particles using convergent light are described. It should be noted that term "particle" is referred herein to a droplet, a bubble, or any other object. The particle can have a spherical shape, a deformed sphere shape, or any other shape. The particle can comprise a liquid, a solid material, a bubble, or any combination thereof.

For an embodiment, a plurality of illuminating light beams propagating on multiple optical paths through a particle field are generated. The plurality of illuminating light beams converge at a measurement volume. A shadow image of a particle passing through a portion of the measurement volume at a focal plane of a digital camera is imaged. Shadow images of other particles in the particle field are removed using the plurality of illuminating light beams.

For an embodiment, converging light is used to produce shadow images of particles passing through a portion of a measurement volume at a focal plane of an imaging system. Shadow images of the particles passing through one portion of the converging light outside the focal plane are eliminated by other portions of the converging light. This approach provides an advantage as it allows the observation of particles without the difficulties associated with obscuration of the light reaching the particles at the measurement volume.

Figure 1:
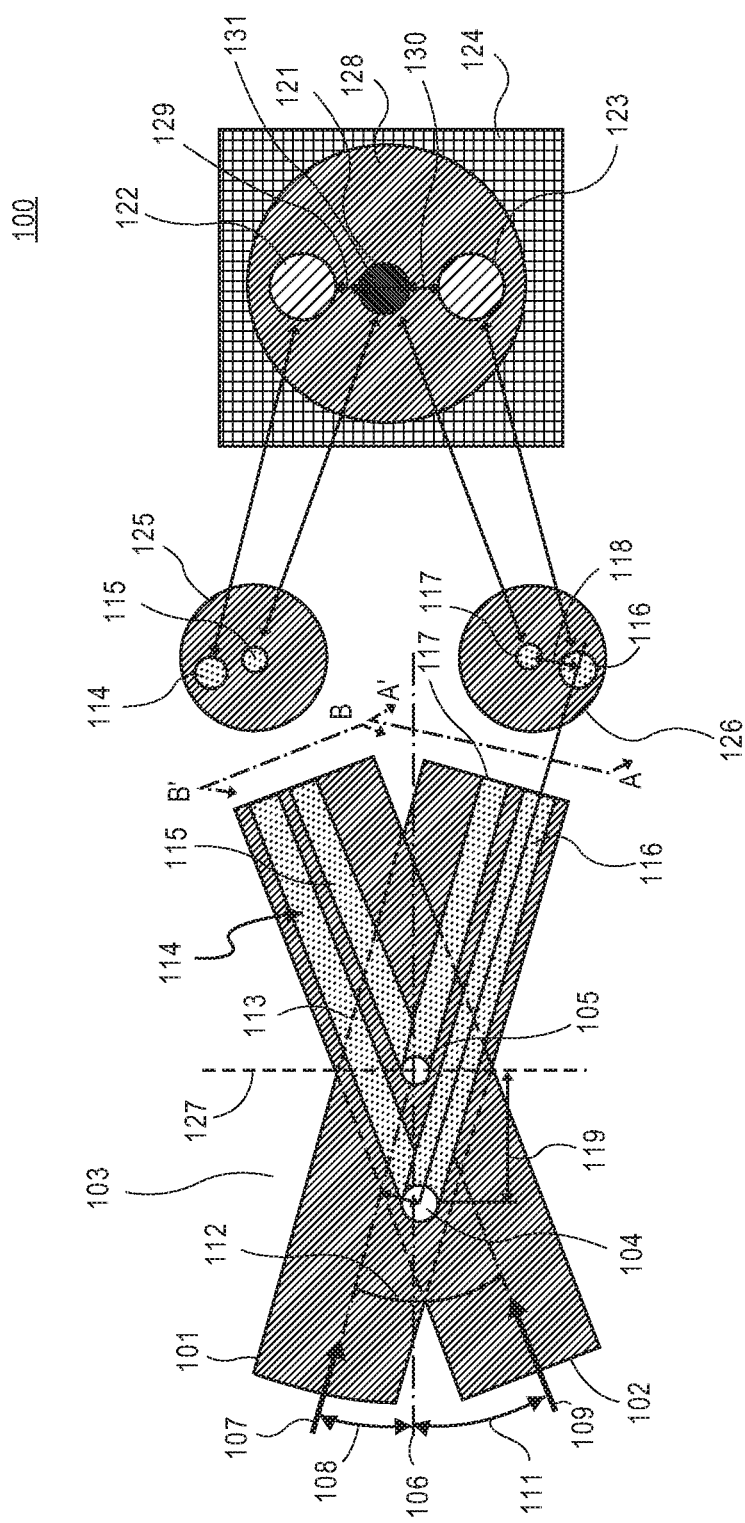
FIG. 1 shows a schematic of one embodiment of an apparatus to image particles.

FIG. 1 shows a schematic of one embodiment of an apparatus to image particles. Apparatus 100 comprises a plurality of illuminating light beams—e.g, an illuminating light beam 101 and an illuminating light beam 102—to eliminate out of focus shadows in an image plane. As shown in FIG. 1, illuminating light beam 101 propagates on an optical path along a direction 107 and illuminating light beam 102 propagates on an optical path along a direction 109 through a particle field 103. The optical path of beam 101 is different from the optical path of beam 102. For an embodiment, a wavelength of beam 101 is different from a wavelength of beam 102. In other words, beams 101 and 102 have different colors. For example, beam 101 is red, or any other color, and beam 102 is green, or any other color different from that of the beam 101. For another embodiment, beams 101 and 102 have the same wavelength. For an embodiment, at least one of the illuminating light beams 101 and 102 is pulsed. For one embodiment, the beams are pulsed in unison to "freeze" the particle motion.

The particle field 103 comprises particles, such as a particle 104 and 105. Illuminating light beam 101 and illuminating light beam 102 converge at a measurement volume 113. As shown in FIG. 1, measurement volume 113 is a region where light beams 101 and 102 overlap with each other. The beam 101 is at an angle 108 to an optical axis 106. The beam 102 is at an angle 111 to optical axis 106. For an embodiment, if one of the angles 108 and 111 is a 0 degree angle, the other one of the angles 108 and 111 can be any angle other than 0 degree. For one embodiment, the beam intersection angle is determined by an f-number (f #) of the imaging system. Generally, the f # is defined as a lens focal length divided by the lens diameter. For another embodiment, each beam is detected by a separate lens and the image transferred to a common image plane so that larger beam intersection angles can be used.

As shown in FIG. 1, illuminating light beams 101 and 102 intersect at an angle 112. For an embodiment, angle 112 is a sum of angles 108 and 111. Particle 105 passes a portion of the measurement volume 113 at a focal plane 127 of an imaging system and produces an individual shadow 115 along direction 109 of beam 102 and an individual shadow 117 along direction 107 of beam 101. Particle 104 passes a portion of the measurement volume 113 at a distance 119 away from focal plane 127 and produces an individual shadow 114 along direction 109 of beam 102 and an individual shadow 116 along direction 107 of beam 101.

A cross-sectional view 126 of a measurement volume 113 along an axis A-A' perpendicular to direction 107 comprises individual shadows 116 and 117. A cross-sectional view 125 of a measurement volume 113 along an axis B-B' perpendicular to direction 109 comprises individual shadows 114 and 115, as shown in FIG. 1. A shadow image 121 of particle 105 is formed on image plane 124 of an imaging system. Shadow image 121 is formed as a superposition of individual shadows 115 and 117. As shown in FIG. 1, shadow image 121 is substantially different from a background 128 produced by beams 102 and 101. An individual shadow image 122 is formed from individual shadow 114 and an individual shadow image 123 is formed from individual shadow 116 on image plane 124. The individual shadow images 122 and 123 of particle 104 do not overlap and are separated from each other and from shadow image 121 on image plane 124. The individual shadow images 122 and 123 of particle 104 are substantially the same as background 128.

Figure 3:
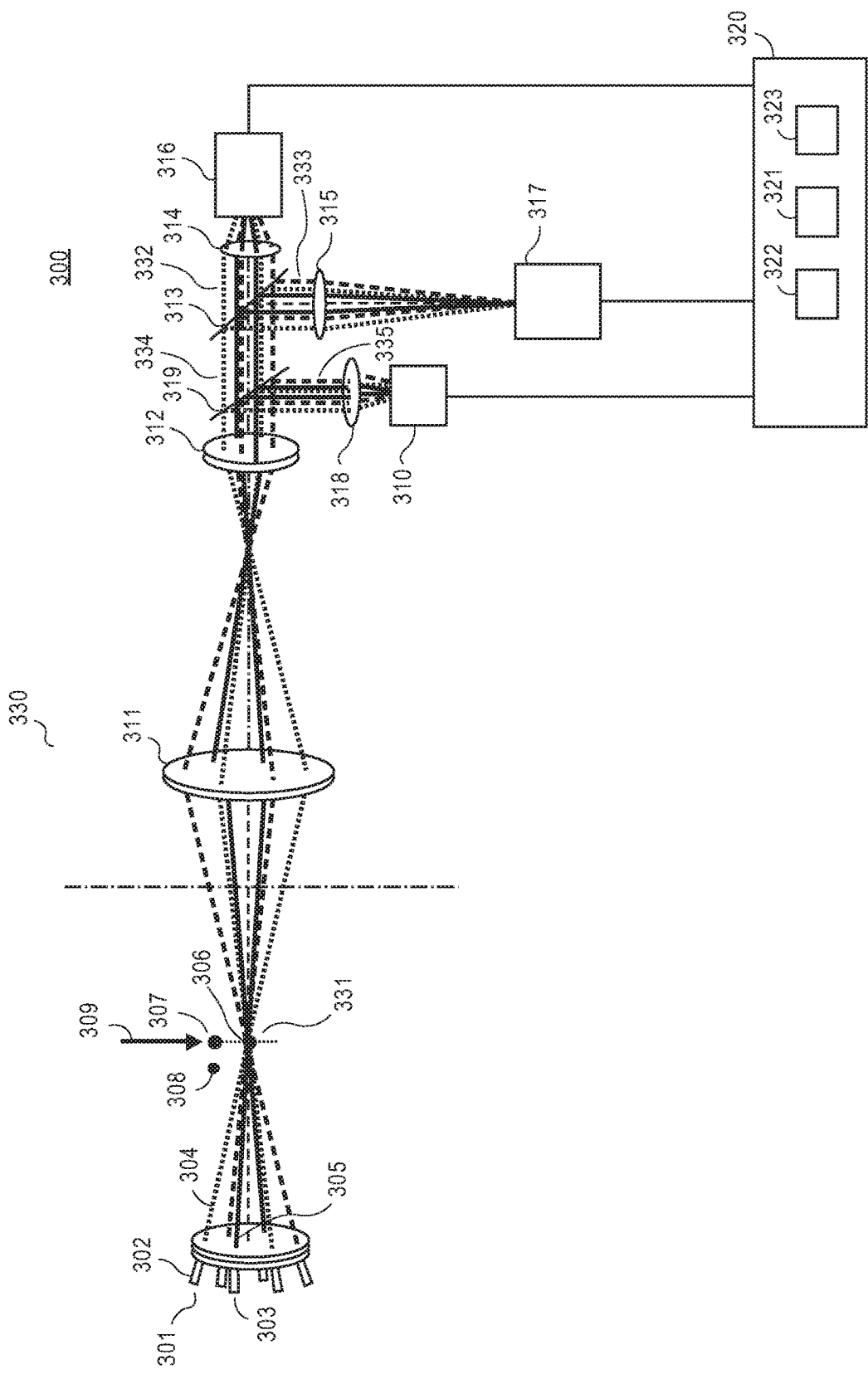
FIG. 3 is a view showing one embodiment of a system to image particles.

For an embodiment, a displacement distance of each of the individual shadow images 122 and 123 from the shadow image 121 indicates that shadows of particles displaced from the focal plane are displaced in the image plane at the camera and will not form deep shadows. The displacement distance in the image plane can be used to estimate the distance of the particles from the focal plane in the sample volume. This information can be used if the particle is in sufficient focus to be sized accurately. For example, a displacement distance 131 between individual shadow images 122 and 123 is determined. For example, a displacement distance 129 between individual shadow image 122 and shadow image 121 on image plane 124 is determined. For example, a displacement distance 130 between individual shadow image 123 and shadow image 121 on image plane 124 is determined. For an embodiment, the focus of shadow image 121 is evaluated based on the distances 129 and 130 to determine a type of the particle. For one embodiment, the type of the particle comprises a particle state—e.g., a liquid, a solid, a bubble in liquid or solid, or any combination thereof. For another embodiment, the type of the particle represents a particle shape, e.g., a spherical, oval, a multi-sided shape—e.g., triangular, rectangular, square, diamond, rhombus, other multi-sided shape, —or any other particle shape. For one embodiment, the particle information comprises a particle velocity, a particle size, or any other particle information. For an embodiment, the size of the particle is at least 0.1 microns ("µm"). For another embodiment, the size of the particle is less than 5 microns ("µm"). For yet another embodiment, the size of the particle is in an approximate range from about 5 µm to about 3000 µm. For an embodiment, a greatest size for the particle is based upon the size of the CMOS array, as the particle fits on the CMOS array. A smallest size for the particle is greater than the size of the pixels. For alternative embodiments, a plurality of different magnifications are used, as shown in FIG. 3.

For an embodiment, at least two illuminating beams crossing at a common point to form the measurement volume are used to image particles. For more specific embodiment, a number of illuminating light beams at a common point to form the measurement volume to image the particles is in an approximate range from 2 to 12. For an embodiment, the illuminating light beams are produced by lasers, light emitting diodes ("LEDs"), or both. For one embodiment, each of the illuminating light beams is produced by a separate inexpensive diode laser and as such, is incoherent with the other beams. For another embodiment, LEDs are used to generate the illuminating light beams. The LEDs advantageously do not produce laser speckle and provide a background that is more homogenous than a laser background. For yet another embodiment, the plurality of illuminating light beams (e.g., a conical beam) are generated by a single light source using axicons, as described in further detail below with respect to FIGS. 10-12. For this embodiment, a single beam is used with an axicon to produce a conical illumination which is equivalent to a continuum of converging beams.

For an embodiment, converging illuminating light beams provide an intense uniform illumination in the measurement volume which resembles white light. Generally, white light produces the best shadow images free from troublesome diffraction. Because each illuminating light beam has a significantly different optical path to the measurement volume, particles that momentarily block parts of any one beam (or region of the conical light produced by an axicon) as they pass through the beams outside of the measurement volume are not correlated or block any of the other beams at the same time and location. Thus, unlike in conventional particle shadow imaging systems with a single beam path through the particle field (e.g., collimated light illumination), the illumination by the converging light at the measurement volume may be reduced slightly but does not significantly lose uniformity of intensity nor is it plagued with out-of-focus shadows from particles outside of the measurement volume. Particles passing the illuminating beams outside the measurement volume do not produce significant shadows because only a small part of the other beams is shadowed at any instant. Thus, even in dense sprays and under conditions with very large drops—e.g., drizzle and rain—the background noise is advantageously minimized. Any non-uniformity in the beam intensity is also advantageously minimized as a result of the overlap of the other beams. A CCD camera, a CMOS camera, or both can be used to capture the images. For an embodiment, all of the illuminating light beams are pulsed for a very short duration so that particle motion does not have an effect on the images. For one embodiment, the pulse duration is from about 10 nanoseconds (nsec) to about 3000 nsec, or any other duration. For another embodiment, the pulse duration depends on the speed of the particles. For another embodiment, the light beams are pulsed twice at a known time separation to form pairs of images which can be used to obtain the particle velocity.

For an embodiment, intersection angle 112 of illuminating light beams 101 and 102 is adjusted to set the measurement volume 113 at the focal plane 127 of the imaging system and to remove the shadow images of the particles outside the measurement volume. Using multibeam illumination with a sufficiently large angle provides an advantage over the conventional systems as it allows the observation of the particles in the focal plane because the illuminating beams are not all blocked by larger particles or other structures in the beam paths.

For an embodiment, a quantity of the illuminating light beams is adjusted to remove the shadow images of the particles that are outside the measurement volume. For an embodiment, a light beam wavelength is adjusted to remove the shadow diffraction on images of the particles in the measurement volume. For an embodiment, the plurality of illuminating light beams are synchronized with the digital camera, as described in further detail below.

For an embodiment, the beam intersection angle determines how rapidly the individual shadow images separate for the particles that are fore and aft of the focal plane of the imaging system. At the same time, the depth of field characteristics of the imaging system determines how rapidly the shadow images move out of focus. Optimization of the multibeam illumination approach requires an analysis of the image separation rate and the imaging system depth of field (DoF). For one embodiment, the intersecting beams enter the camera lens and are imaged to the camera focal plane which requires that the f # (a focal length divided by a lens diameter) match the beam intersection angle. For another embodiment, a separate lens for each beam is used with mirrors that direct the beams and shadow images onto the CCD or CMOS array.

Typically, for particle sizing, the acceptable size uncertainty sets the depth of field of the imaging system. Observations of larger structures such as spray breakup generally will allow a larger circle of confusion and hence, a greater depth of field for the imaging system. For single beam illumination, the shadow image going out of focus blurs at the edges but remains as a single image. With multibeam illumination, the individual shadow images of the particle both blur and separate as they go out of focus. This information is used to aid in the determination if the shadow images are in a focus or are unacceptably out of the focus.

For an embodiment, when using the multibeam illumination, the rate of separation of the individual shadow images of the particle as the particle is moved away from the focal plane of the imaging system is estimated. With the multibeam illumination approach, there is additional information to be considered when determining whether a particle is in a focus. The separation of the images changes the image density gradient. The density gradient at the edge of the shadow image of the particle is affected by the degree of separation of individual shadow images with the distance of the particle from the focal plane. At the same time, the individual shadow images are expanding due to going out of focus with distance from the focal plane. For an embodiment, as density of the particles increases, decreasing a focal number ("f #") of the imaging system, increasing an intersection angle of the illuminating light beams, or both are used to eliminate the disturbances from shadows produced by particles passing the beams outside of the focal plane.

Figure 2:
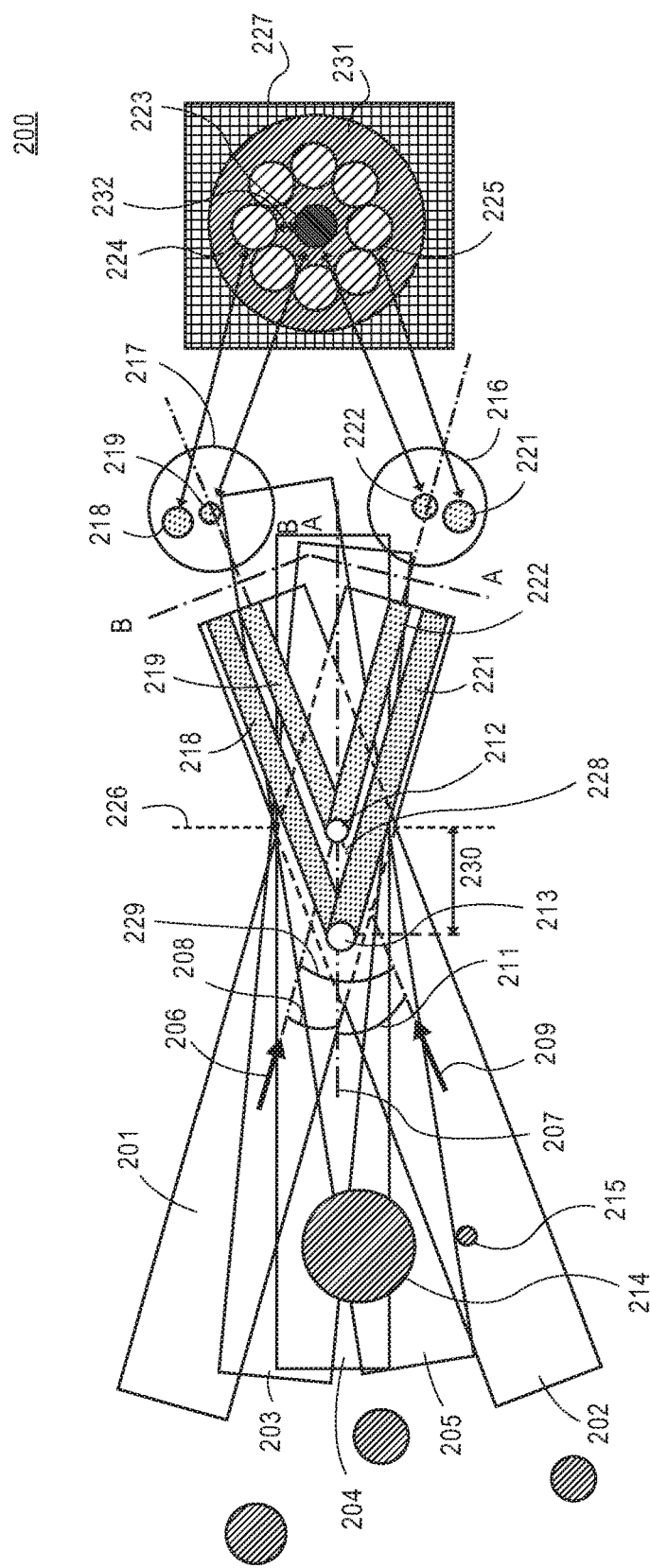
FIG. 2 shows a schematic of another embodiment of an apparatus to image particles.

FIG. 2 shows a schematic of another embodiment of an apparatus to image particles. Apparatus 200 comprises a plurality of illuminating light beams—e.g, an illuminating light beams 201, 202, 203, 204, and 205—to eliminate out of focus shadows in an image plane. Each of the illuminating light beams 201, 202, 203, 204, and 205 propagates on a respective optical path along a respective direction through a particle field comprising particles, such as particles 212 and 213. For example, illuminating light beam 201 propagates on an optical path along a direction 206 and illuminating light beam 202 propagates on an optical path along a direction 209. For an embodiment the optical paths of the illuminating light beams 201, 202, 203, 204, and 205 are different. For an embodiment, the wavelengths of the illuminating light beams 201, 202, 203, 204, and 205 are different. In other words, the illuminating light beams 201, 202, 203, 204, and 205 have different colors. For example, beam 201 is red, beam 202 is green, beam 203 is blue, beam 204 is yellow, beam 205 is purple, or any other color different from each other. For an embodiment, at least one of the illuminating light beams 201, 202, 203, 204, and 205 is pulsed. Particles 212 and 213 represent particles 104 and 105.

Illuminating light beams 201, 202, 203, 204, and 205 converge to form a measurement volume 228 at a focal plane 226 of an imaging system. Measurement volume 228 is a region where all illuminating light beams 201, 202, 203, 204, and 205 overlap, as shown in FIG. 2. The illuminating light beams 201, 202, 203, 204, and 205 intersect with each other at multiple angles. Each of the illuminating light beams 201, 202, 203, 204, and 205 is at a respective angle to an optical axis 207. As shown in FIG. 2, the beam 201 is at an angle 208 to an optical axis 207. The beam 202 is at an angle 211 to optical axis 207. For an embodiment, if one of the illuminating light beams 201, 202, 203, 204, and 205 is at a 0 degree angle to optical axis 207, other ones of the illuminating light beams 201, 202, 203, 204, and 205 can be at any angle other than 0 degree to optical axis 207.

As shown in FIG. 2, illuminating light beams 201 and 202 intersect at an angle 229. For an embodiment, angle 229 is a sum of angles 208 and 211. Particle 212 passing a portion of the measurement volume 228 at focal plane 226 produces a plurality of individual shadows from each of the illuminating light beams 201, 202, 203, 204, and 205, such as an individual shadow 219 from beam 202 and an individual shadow 222 from beam 201. Particle 213 passing a portion of the measurement volume 228 at a distance 230 away from focal plane 226 produces a plurality of individual shadows from each of the illuminating light beams 201, 202, 203, 204 and 205, such as an individual shadow 218 from beam 202 and an individual shadow 221 from beam 201. A cross-sectional view 216 of a measurement volume 228 along an axis A-A' perpendicular to direction 206 comprises individual shadows 221 and 222. A cross-sectional view 217 of a measurement volume 228 along an axis B-B' perpendicular to direction 209 comprises individual shadows 219 and 218, as shown in FIG. 2. A shadow image 223 of particle 212 is formed on an image plane 227 of an imaging system. Shadow image 223 is formed as a superposition of individual shadows—e.g., such as 115 and 117—from each of the illuminating light beams 201, 202, 203, 204, and 205. As shown in FIG. 2, shadow image 223 is substantially different from a background 231 produced by the illuminating light beams 201, 202, 203, 204, and 205. Individual shadow images are formed from individual shadows on image plane 227, such as individual shadow images 224 and 225. For example, individual shadow image 224 is formed from individual shadow 218 and individual shadow image 225 is formed from individual shadow 216. Each of the individual shadow images is removed from shadow image 223 on image plane 124 by a distance, such as a distance 232. The individual shadow images of particle 213 do not overlap and are separated from each other by a distance on image plane 227. The individual shadow images of particle 213 are substantially the same as background 231.

For an embodiment, the illuminating light beams are produced by lasers, light emitting diodes ("LEDs"), or both. For one embodiment, each of the illuminating light beams is produced by a separate inexpensive diode laser and as such, is incoherent with the other beams. For another embodiment, LEDs are used to generate the illuminating light beams. For yet another embodiment, the plurality of illuminating light beams are generated by a single light source using axicons, as described in further detail below with respect to FIGS. 10-12. For an embodiment, the illuminating light beams are synchronized with the digital camera, as described in further detail below. For an embodiment, one or more intersection angles of the illuminating light beams are adjusted to set the measurement volume 228 at the focal plane 226 of the imaging system and to remove the shadow images of the particles outside the measurement volume 228. For an embodiment, a quantity of the illuminating light beams of illuminating light beams is adjusted to remove the shadow images of the particles outside the measurement volume 228. For an embodiment, a light beam wavelength is adjusted to reduce the diffraction from the shadow images of the particles inside the measurement volume 228.

An embodiment, displacement distances between the individual shadow images are determined to evaluate a focus of shadow image 223 on image plane. For an embodiment, the focus of shadow image 223 is evaluated based on the displacement distances to determine a particle information, as described above with respect to FIG. 1.

Multi-beam, multidirectional illumination of particles advantageously limits the depth of field of the imaging system as well as eliminates shadows from particles (e.g., droplets, ligaments, and others structures) in the optical beam path outside of the focal volume. As shown in FIGS. 1 and 2, shadows produced on one beam are eliminated by the other beams except at the overlap region of the beams that coincides with the focal plane of the imaging system. Depending on the particle and spray structure density, the beam intersection angle can be set to limit the shadows to relatively narrow region or they can be set at a very shallow angle to allow depth of beam overlap that coincides with the imaging system (e.g., camera) depth of field. The beam intersection angle may be limited by the camera lens f # (focal length divided by diameter). For an embodiment, multi-angular illumination is provided by a plurality of laser diodes that can be pulsed synchronously with pulse duration of 10 to 1000 ns, depending on the particle speed. This provides sufficient illumination for imaging the spray droplets, ligaments, and other spray structures. Depending upon the beam extinction, more laser power may be required. Because the diode lasers are relatively inexpensive, any number of the diode lasers can be used to provide sufficient illumination of the particle field. For another embodiment, light emitting diodes (LEDs) are used to provide an illumination area that is greater than the illumination area provided by the laser diodes.

For an embodiment, laser pulse durations from about 10 ns to about 20 ns are used to image particles (e.g., droplets and other structures) moving at typical speeds. For an embodiment, the laser pulse durations in an approximate range from about 10 ns to about 300 ns are provided by Nd:YAG pulse lasers or other common pulse lasers. Such laser pulse durations is used for imaging small regions of a spray—e.g., a few millimeters on a side. For macroscopic imaging the maximum pulse duration may be in an approximate range from about 100 ns to about 2000 ns, depending on the speed of the particles. These pulse durations can provided by arrays of inexpensive LEDs. Pulse durations are typically determined by the speed of the particles to prevent or minimize blur. For example, particles moving at 100 m/s may have only a 2 micron blur at 20 ns pulse duration. If the particle is moving at 1 m/s, a 300 ns pulse may only cause a 0.3 microns blur.

For an embodiment, a camera array of the imaging system does not limit the illumination pulse duration. This advantageously frees a user from the expense and stringent timing demands required by ballistic imaging.

FIG. 3 is a view 300 showing one embodiment of a system 300 to image particles. A system 300 comprises a transmitter system 301 and a receiver system 330. Transmitter system 301 includes one or more light sources—e.g., a light source 302 and a light source 303—generating a plurality of illuminating light beams—e.g., an illuminating light beam 304 and an illuminating light beam 305 propagating on multiple optical paths through a particle field comprising particles—e.g., particles 306, 307, and 308 moving along a direction 309. The illuminating light beams converge to form a measurement volume at a focal plane 331 of an imaging system. The illuminating light beams of FIG. 3 are represented by the illuminating light beams of FIGS. 1 and 2.

For an embodiment, the light sources of the transmitter system 301 comprise lasers, light emitting diodes ("LEDs"), or both, as described above with respect to FIGS. 1 and 2. For another embodiment, the plurality of illuminating light beams are generated by a single light source using axicons, as described in further detail below with respect to FIGS. 10-12. For an embodiment, transmitter system 301 comprises a light source to generate a triggering light beam (not shown). For an embodiment, the triggering light beam is sent to generate a plurality of illuminating light beams, if the particle is detected in the measurement volume, as described in further detail below.

Receiver system 330 comprises an imaging optics and one or more digital cameras to provide a shadow image of the particle 306 passing through the measurement volume at focal plane 331, as described above. For one embodiment, multiple digital cameras—e.g., digital cameras 316, 317 and 310—are used adjust a dynamic range of the particles. For one embodiment, the size dynamic range of the particles is about 300:1.

As shown in FIG. 3, the imaging optics of the receiver system 330 comprises one or more receiver lenses 311 to receive the individual shadows of the particle 306 from each of the illuminating light beams, as described above. One or more image transfer lenses 312 transfer individual shadow images of the particle 306 to a beam splitter 314. Beam splitter 314 splits the illuminating light beams comprising the individual shadow images of the particle 306 into a portion 332 and a portion 333. Portion 332 is sent to one or more focusing lenses 314 to form a shadow image of the particle 306 on an image plane of a digital camera 316. Portion 333 is sent to one or more focusing lenses 315 to form a shadow image of the particle 306 on an image plane of a digital camera 317. The imaging system can optionally comprise a beam splitter 319 to split the illuminating light beams comprising the individual shadow images of the particle 306 into a portion 334 and a portion 335. In this case, portion 334 is sent to beam splitter 313 to form a shadow image of the particle 306 on corresponding image planes of digital cameras 316 and 317. Portion 335 is sent to one or more focusing lenses 318 to form a shadow image of the particle 306 on an image plane of a digital camera 310. For one embodiment, the multiple camera approach is used to allow different magnifications to enable sizing particles with high resolution over a wide size range.

A processing system 320 is coupled to the receiver system 330. Processing system 320 comprises a processor 321, a memory 322, and a display 323 to display shadow images of the particles passing through the measurement volume. For another embodiment, the processor 321 is configured to determine one or more displacement distances of the individual shadow images produced by each of the plurality of illuminating light beams and to determine a focus of the shadow image using the displacement information, as described in further detail below. For another embodiment, the processor 321 is configured to detect the shadow image, to evaluate a depth of field of the particle, a focus of the particle, or both based on the shadow image to determine a type of the particle based on the evaluation, and to determine particle information based on the type of the particle, as described in further detail below.

For one embodiment, the size range of the imaging system is extended to cover a dynamic size range of from 0.05 µm to 3000 µm. This can be accomplished with high resolution and very efficient image capture and transfer to the image processing computer using different magnifications and separate CMOS cameras.

Because of the requirement to achieve a relatively high rate of image capture (greater than 100 per second), a high resolution CCD camera may not be appropriate because transferring each image would take too long and the storage required may become prohibitively high. The system having a plurality of digital cameras, as depicted in FIG. 3, has separate staging of the image magnification while maintaining high resolution. In this way, the particle images can nearly fill the image space of the camera over the entire size range. The goal of reaching a size dynamic size range of 5 to 3000 µm or larger without needing to patch data together from separate instruments is achieved.

To ensure that only in-focus particles are captured by the imaging system, a particle triggering system can be optionally used, as described in further detail below. For an embodiment, the triggering response is an integral part of the determination of the measurement volume size. Being able to accurately characterize the measurement volume allows the determination of the particle information, for example, particle concentration, liquid water content, particle size distributions that are corrected for change in apparent depth of field as a function of particle size, or other particle information.

Figure 4A:
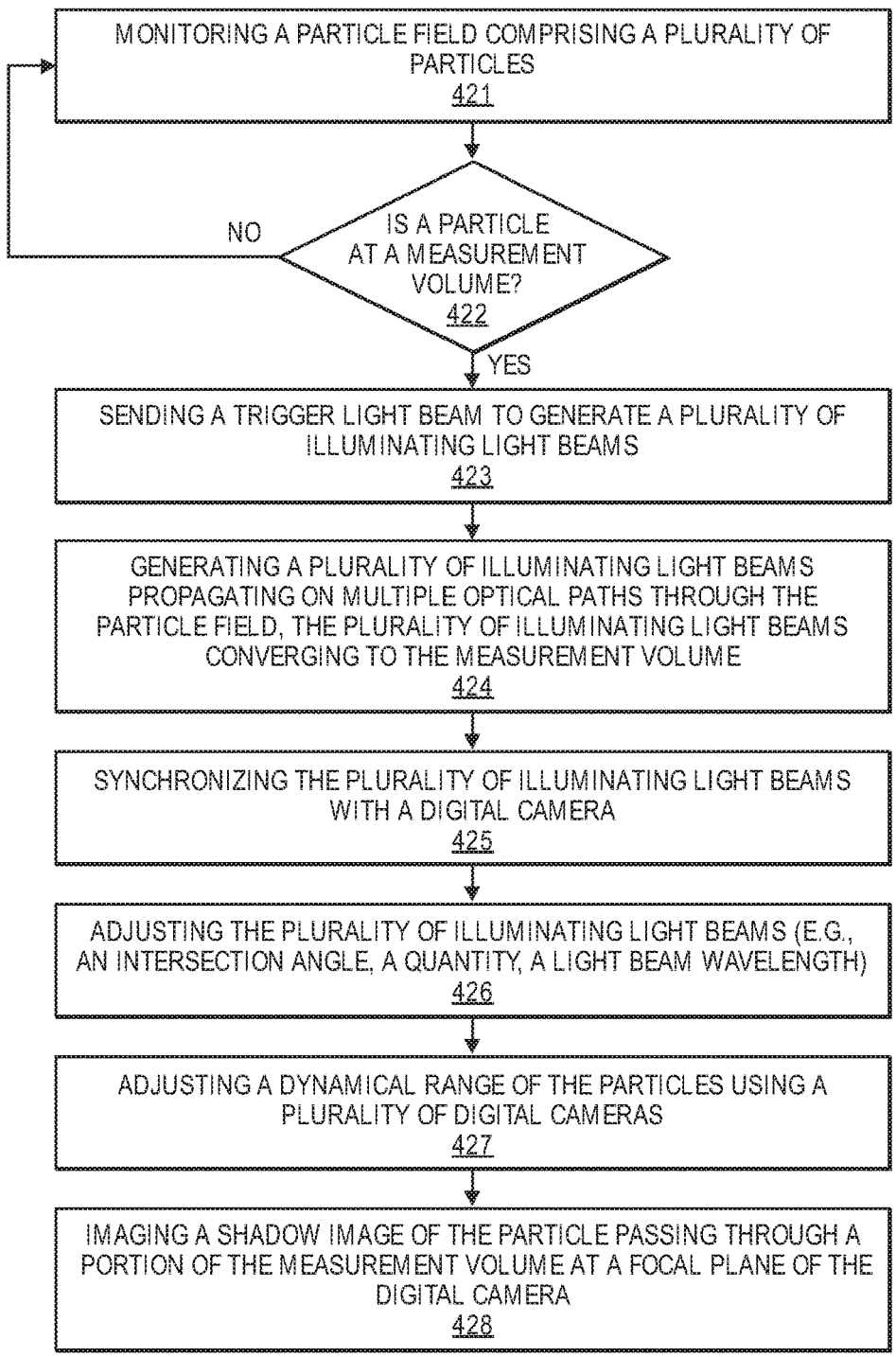
FIG. 4A shows a flow chart of one embodiment of a method to image particles.

FIG. 4A shows a flow chart of one embodiment of a method 420 to image particles. At operation 421 a particle field comprising a plurality of particles is monitored. For one embodiment, the particle field is monitored using a triggering light beam. At operation 422 it is determined if a particle is at a measurement volume. If the particle is not in a measurement volume, method goes back to operation 421. If the particle is in the measurement volume, at operation 423 a triggering light beam is sent to generate a plurality of illuminating light beams. For one embodiment, the triggering light beam is used to pulse the lasers synchronously with the camera shutter to sample only when a particle is present. For another embodiment, the lasers and camera are triggered simultaneously at a fixed rate. In this case, a plurality of illuminating light beams synchronized with a camera shutter are generated at a fixed rate independent of whether the particles are present at the measurement volume. For an embodiment, the system is set up by adjusting the laser fluence (an amount of light produced per pulse), the camera gain to ensure a shadow contrast is greater than a predetermined contrast, and the number of cameras to be used prior to the measurement. For one embodiment, the cameras and magnifications are preset before the measurement data acquisition. At operation 424, in response to receiving the trigger signal, the plurality of illuminating light beams propagating on multiple optical paths through a particle field are generated. The plurality of illuminating light beams converge at the measurement volume, as described above with respect to FIGS. 1-3. At operation 425 the plurality of illuminating light beams are synchronized with a digital camera. At operation 426 the parameters of the illuminating light beams—e.g., an intersection angle, a quantity, a light beam wavelength—are adjusted to remove the shadow images of the particles outside the measurement volume, as described above. For another embodiment, the parameters of the illuminating light beams—e.g., an intersection angle, a quantity, a light beam wavelength—are adjusted during the design of the optics. At operation 427 a dynamical range of the particles is adjusted using a plurality of digital cameras, as described above. It should be noted that operations 426 and 427 can be performed in any order. For an embodiment, operation 427 is after operation 426. For another embodiment, operation 426 is after operation 427. At operation 428 imaging of a shadow image of the particle passing a portion of the measurement volume at a focal plane of the digital camera is performed, as described above. For one embodiment, processor 321 is configured to perform method 420.

Figure 4B:
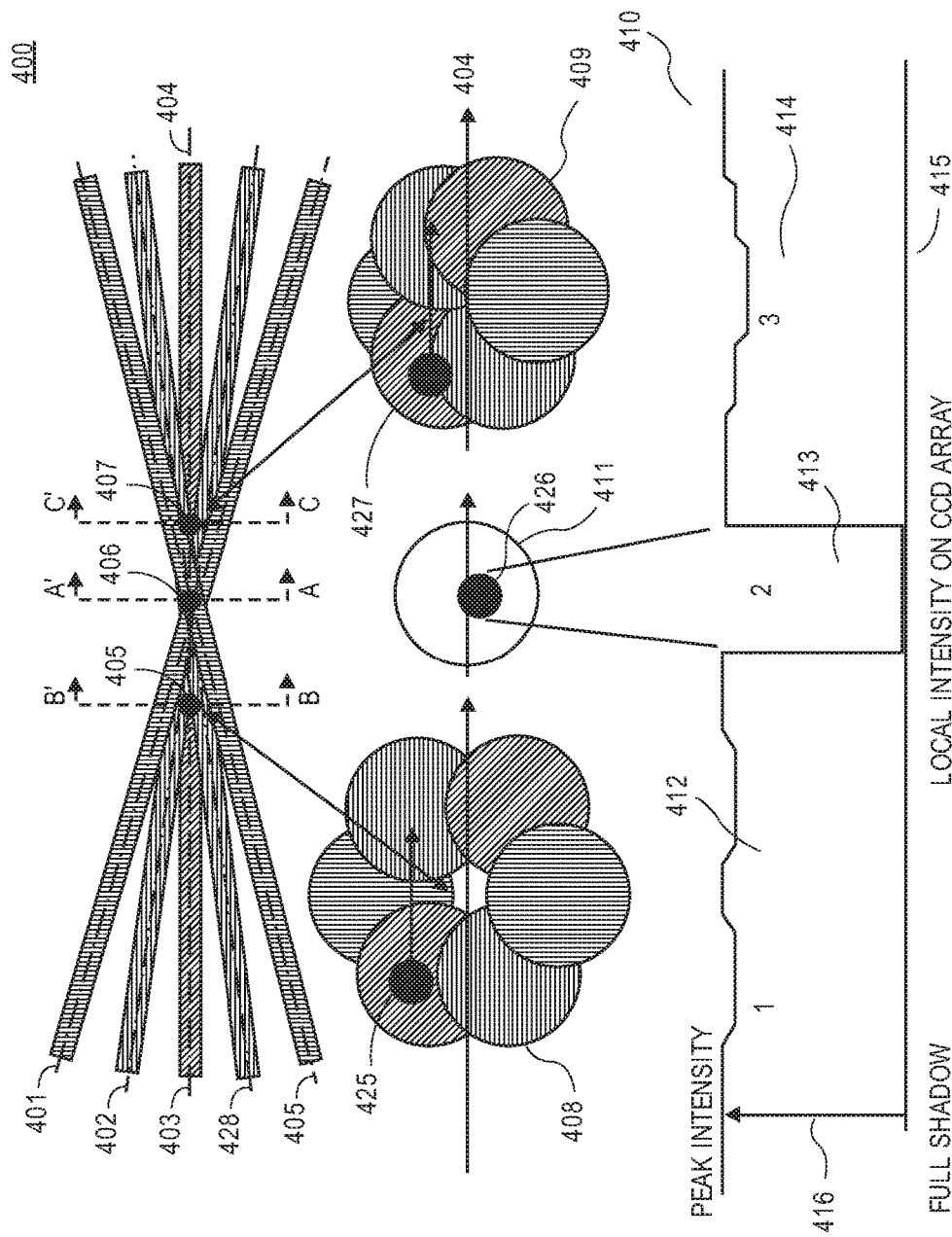
FIG. 4B is a view illustrating one embodiment of a multiple wavelength, multiple angle illumination to produce high quality shadow images.

FIG. 4B is a view 400 illustrating one embodiment of a multiple wavelength, multiple angle illumination to produce high quality shadow images even in a dense particle field environment. A plurality of illuminating light beams—e.g., illuminating light beams 401, 402 403, 428, and 429—propagate on respective optical paths along respective directions through a particle field comprising particles, such as particles 405, 406, and 407. Particles 405, 406, and 407 represent particles described above with respect to FIGS. 1-4A. For one embodiment, the illuminating light beams have the wavelengths that are different from each other. For another embodiment, some illuminating light beams have one wavelength, and some other illuminating light beams have other wavelengths. For example, illuminating light beams 401 and 429 can have one wavelength, (e.g., red), illuminating light beams 402 and 428 can have another wavelength (e.g., blue) and illuminating light beam 403 can have yet another wavelength different (e.g., green). The illuminating light beams converge to form a measurement volume at a focal plane of an imaging system. The focal plane of the imaging system propagates along an axis A-A'. The measurement volume is a region where all of the illuminating light beams overlap, as shown in FIG. 4B.

Particle 406 passing a portion of the measurement volume at the focal plane of the imaging system produces a plurality of individual shadows from each of the illuminating light beams that overlap to form a shadow image 426 of the particle 406 on the image plane of the imaging system. A cross-sectional view 411 of the measurement volume along the axis A-A' perpendicular to an optical axis 404 comprises the shadow image 426. Particle 405 passing illuminating light beam 403 before the focal plane A-A' produces an individual shadow 425 from the illuminating light beam 403. Particle 405 does not produce shadows from other illuminating light beams, such as illuminating light beams 401 and 402. A cross-sectional view 408 of the illuminating light beams along an axis B-B' perpendicular to optical axis 404 comprises individual shadow 425 caused by beam 403. Particle 407 passing illuminating light beams 403 and 428 after the focal plane A-A' produces an individual shadow 427 from the illuminating light beams 403 and 428. Particle 407 does not produce individual shadows from other illuminating light beams, such as illuminating light beams 401 and 402. A cross-sectional view 409 of the illuminating light beams along an axis C-C' perpendicular to optical axis 404 comprises shadow 427 that is a superposition of the individual shadows caused by beams 403 and 428.

A graph 410 illustrates one embodiment of light intensity 416 versus a distance on a CCD array 415. The light intensity 416 varies from a peak intensity to a full shadow, as shown in graph 410. The peak intensity corresponds to a background condition when there is no particle that crosses at least one of the beams. As shown in graph 410, light intensity of the shadow image 426 of the particle 406 in a region 413 of the CCD array is substantially lower than the light intensity in a region 412 and a region 414 of the CCD array. That is, the shadow image of particle 406 is substantially different from the background peak light intensity and from the light intensity of the individual shadow images 425 and 427.

As shown in FIG. 4B, the illuminating light beams converge at the measurement volume to emulate white light illumination. For one embodiment, color CCDs (RGB) are used to extract color information on the shadow image. Color information can provide additional dimensional information on the particle shadows. Delays between various color illuminations can also be used to measure velocity (analogous to double pulsing a single laser). For one embodiment, double pulse imaging is implemented to provide shadow particle image velocimetry (PIV) images to obtain droplet and spray structure size and velocity. The duration of the one or more illumination pulses is naturally limited by the resolution of the imaging system and the speed of the target particle. For one embodiment, for a microscopic imaging, a maximum pulse duration of about 20 ns is used (2 µm blur at 100 m/s). For example, if the particle is moving at 100 m/s, it will move 2 µm in 20 ns. This will blur the edges by 2 microns. For smaller particles, shorter pulse duration is used to minimize blur.

FIG. 5A1 is a view 500 showing examples of five-beam illumination images acquired in a relatively dense spray (about 5,000/cc). A five-beam illumination image 501 shows shadow images of the particles passing the measurement volume at a focal plane of the imaging system. The shadow images, e.g., a shadow image 503 are in-focus and are substantially separate from a background 504 and from individual shadow images of other particles outside the focal plane of the imaging system, such as an individual shadow image 505. As shown in image 501, the shadow images, such as shadow image 503 are only formed in the image plane of the particle where the illuminating light beams overlap at the focal plane of the imaging system. The individual shadow images from some individual beams of the particles passing the beams outside the focal plane—e.g., individual shadow image 505—are illuminated by other illuminating light beams, so that the full shadow images of such particles are not produced that significantly simplifies the detection and measurement of the in focus particle shadow images, such as shadow image 503. For one embodiment, parameters of the illuminating light beams, such as an intersection angle, a number of beams, and wavelengths are optimized to prevent the individual shadow images of the particles outside the focal plane from being formed. A five-beam illumination image 502 shows shadow images of the particles passing the measurement volume outside a focal plane of the imaging system. The shadow images, e.g., a shadow image 506 are out-of-focus, and are not substantially separate from a background 507 and from individual shadow images of other out-of-focus particles, such as an individual shadow image 508.

FIG. 5A2 is a view 510 showing examples of multi-beam illumination images of particles that pass the measurement volume at different distances from the focal plane of the imaging system. As shown in FIG. 5A2, the shadow images of the particle formed by the each of the illuminating beams move away from each other as the particle moves away from the focal plane of the imaging system. An image 511 shows shadow images of the particles passing the measurement volume at a focal plane of the imaging system. As shown in image 511, the individual shadow images of the particle formed by each of the illuminating beams fully overlap to form a shadow image 521 that is substantially separate from the background. An image 512 shows the shadow images of the particles passing the measurement volume at about 100 µm away from the focal plane of the imaging system. As shown in image 512, the individual shadow images of the particle from each of the illuminating beams overlap only partially (about 75%) resulting in a shadow image 522 that is more blurred and less separate from the background than image 521. An image 513 shows the shadow images of the particles passing the measurement volume at about 200 µm away from the focal plane of the imaging system. As shown in image 513, the shadow images of the particle from each of the illuminating beams overlap only about 50% resulting in a shadow image 522 that is more blurred and less separate from the background than image 522.

Figure 5B:
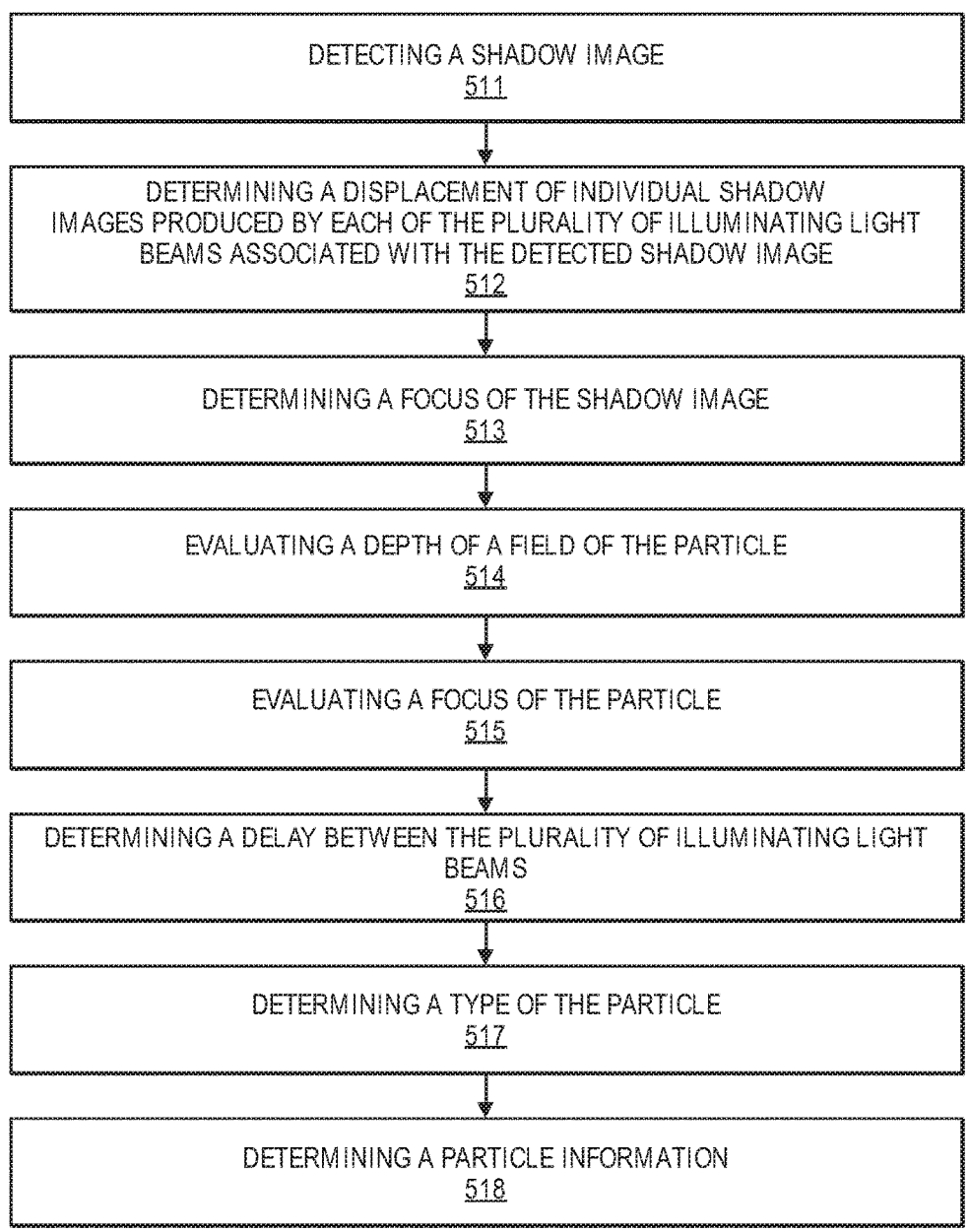
FIG. 5B shows a flow chart of one embodiment of a method to characterize particles.

FIG. 5B shows a flow chart of one embodiment of a method 510 to characterize particles. At operation 511 a shadow image is detected. At operation 512 a displacement of individual shadow images produced by each of the plurality of illuminating light beams associated with the detected shadow image is determined. At operation 513 a focus of the shadow image is determined. At operation 514, a depth of field of the particle associated with the shadow image is evaluated. At operation 515, a focus of the particle is evaluated. At operation 516, a delay between the plurality of illuminating light beams is determined. At operation 517, a type of the particle is determined. For an embodiment, the type of the particle is determined based on at least on one of the operations 512 to 516.

For an embodiment, the type of the particle represents a particle's state—e.g., liquid, solid, a bubble in liquid, or any combination thereof. For another embodiment, the type of the particle represents a particle shape—e.g., (1) spherical, (2) oval, (3) multi-sided shape (e.g., triangular, rectangular, square, diamond, rhombus, other multi-sided shape), or (4) other particle shape. At operation 518 a particle information is determined. For an embodiment, the particle information is determined based on the type of the particle. For another embodiment, the particle information is determined based at least on one of the operations 512 to 516. For one embodiment, the particle information comprises a particle velocity, a particle size, or any other particle information.

Figure 6:
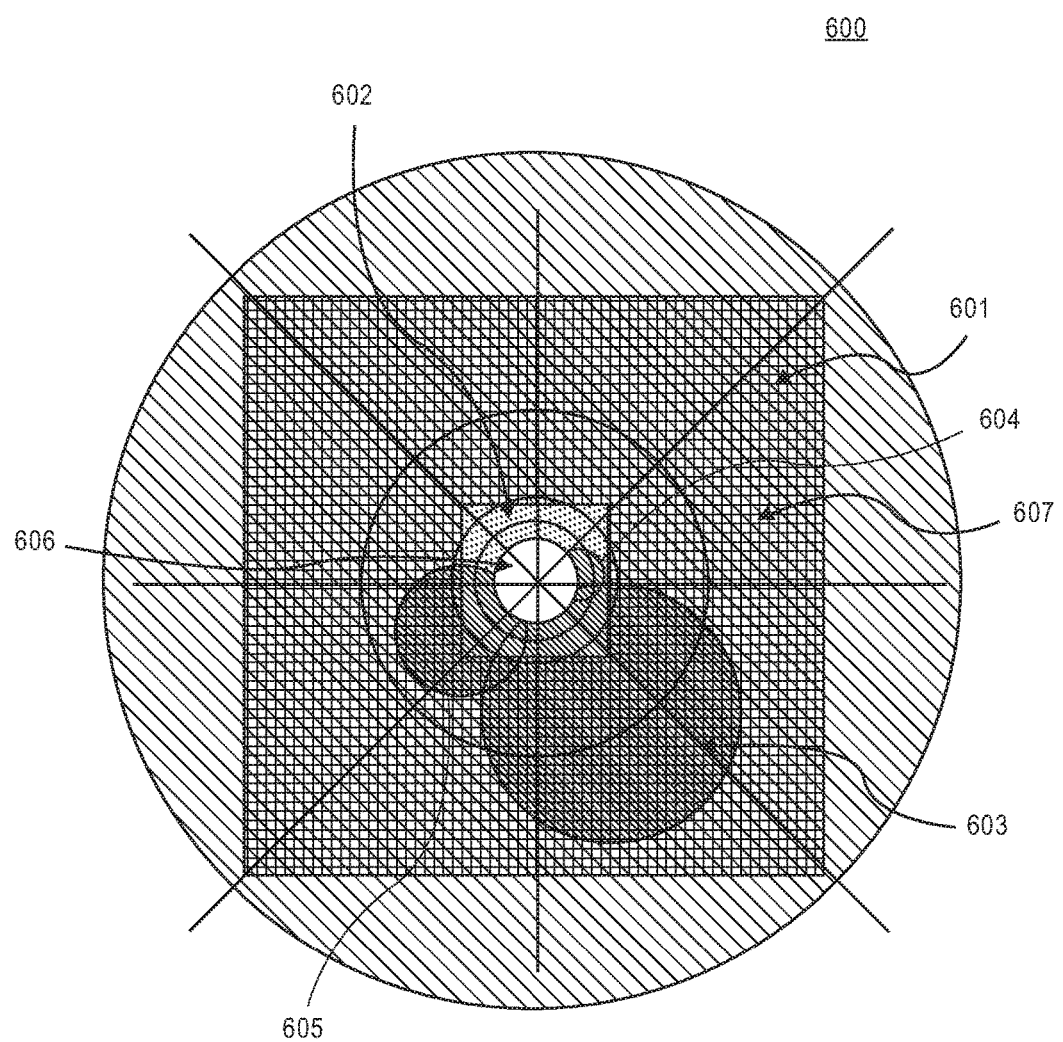
FIG. 6 is a view showing one embodiment of images of two CCD arrays superimposed on a measurement volume according to one embodiment of the invention.

FIG. 6 is a view 600 showing one embodiment of images of two CCD arrays superimposed on a measurement volume. As shown in FIG. 6, particles having different sizes—such as particles 603, 604, and 605—that pass a measurement volume 607 formed by overlapping illuminating light beams are imaged by multiple CCD arrays. Particles 603, 604, and 605 are detected by a triggering light beam 606. The size of the particle 603 is larger than that of particle 605. Particle 605 is larger than that of particle 604. As shown in FIG. 6, small particles—e.g., particle 604—are imaged by a field of view 602 of a CCD1 array. Large particles—e.g., particle 603—are imaged by a field of view 601 of a CCD2 array. Medium particles—e.g., particle 605 are imaged by the field of view 602 of the CCD1 array and field of view 602 of the CCD1 array. For an embodiment, field of view 601 represents the field of view of the digital camera 316, and field of view 602 represents the field of view of the digital camera 317.

It is possible to obtain a high resolution CCD camera that provides an adequate resolution over a desired particle size range. The field of view for the camera however, needs to be large to encompass all images including the images of the largest particles in the measurement volume. At the same time, it the CCD camera needs to provide a sufficient resolution to image small particles in the measurement volume. For example, CCD cameras that have up to 12 megapixel resolution are available. Transferring and processing such large volumes of data are very time consuming. The data transfer and processing rates to image particles increase to about 1000 image frames per second by using multiple CCD cameras with a triggering system. Using the particle triggering system described in further detail below, the primary drop image can be centered for every frame. Thus, the use of available CCD pixel space is optimized.

Referring back to FIG. 3 and FIG. 6, the first imaging system comprising a first digital camera (e.g., the digital camera 316) observes a magnified image of the particles passing through the image beams at the center of the measurement volume (CCD1 field of view 601). The images of the small particles are recorded on the first digital camera. A beam splitter—e.g., beam splitter 313—and a second imaging system comprising a second digital camera—e.g., digital camera 317—with magnification lower than the magnification of the first digital camera is used to cover a larger area of the particle space to image large particles passing the measurement volume. The images of the large particles are recorded on the second digital camera. Using this strategy, a significant reduction in the number of pixels of information needed to achieve high resolution and accuracy is realized.

Based on the number of pixels in the CCD array, various levels of resolution may be obtained. For example, a 512 pixel CCD array provides resolution of approximately 2 µm per pixel given a field of view that allows complete detection of all particles detected by the trigger of the imaging system. In this case, for the small particles having the diameter size in the approximate range of 10 µm to 500 µm, a measurement volume area of about 1 mm×1 mm is imaged by the camera. For the large particles, the cross-sectional area at the measurement volume imaged is approximately 5 mm by 5 mm and the resolution with a 512 pixel CCD is about 10 µm per pixel. With this approach, approximately 260K pixels of information are transferred from each camera for each trigger event. To attain the same resolution with a single CCD camera, the CCD array needs to be 10 times larger on each side that means that 5120 by 5120 pixel array may be required and about 26 megapixels of information needs to be transferred with each image. In this case, processing the images may require scanning information to determine where the shadowed pixels are and then selecting only that region for processing.

The imaging system comprising multiple separate CCD cameras with beam splitters, as depicted in FIG. 3, provides both high resolution and efficient data transfer and processing. For an embodiment, the triggering system is configured such that particles in a given size range trigger a specific camera instead of triggering all cameras simultaneously. For one embodiment, multiple threshold levels are set on the detector system that trigger corresponding digital cameras. For one embodiment, if the trigger signal is greater than a predetermined amplitude threshold, a digital camera to image particles of a first size range is triggered. If the trigger signal is smaller than a predetermined threshold, a digital camera to image particles of a second size range is triggered. For more specific embodiment, if the trigger signal is greater than a predetermined amplitude threshold, a digital camera to image the smaller particles is triggered. If the trigger signal is smaller than a predetermined threshold, a digital camera to image the larger particles is triggered.

Figure 7:
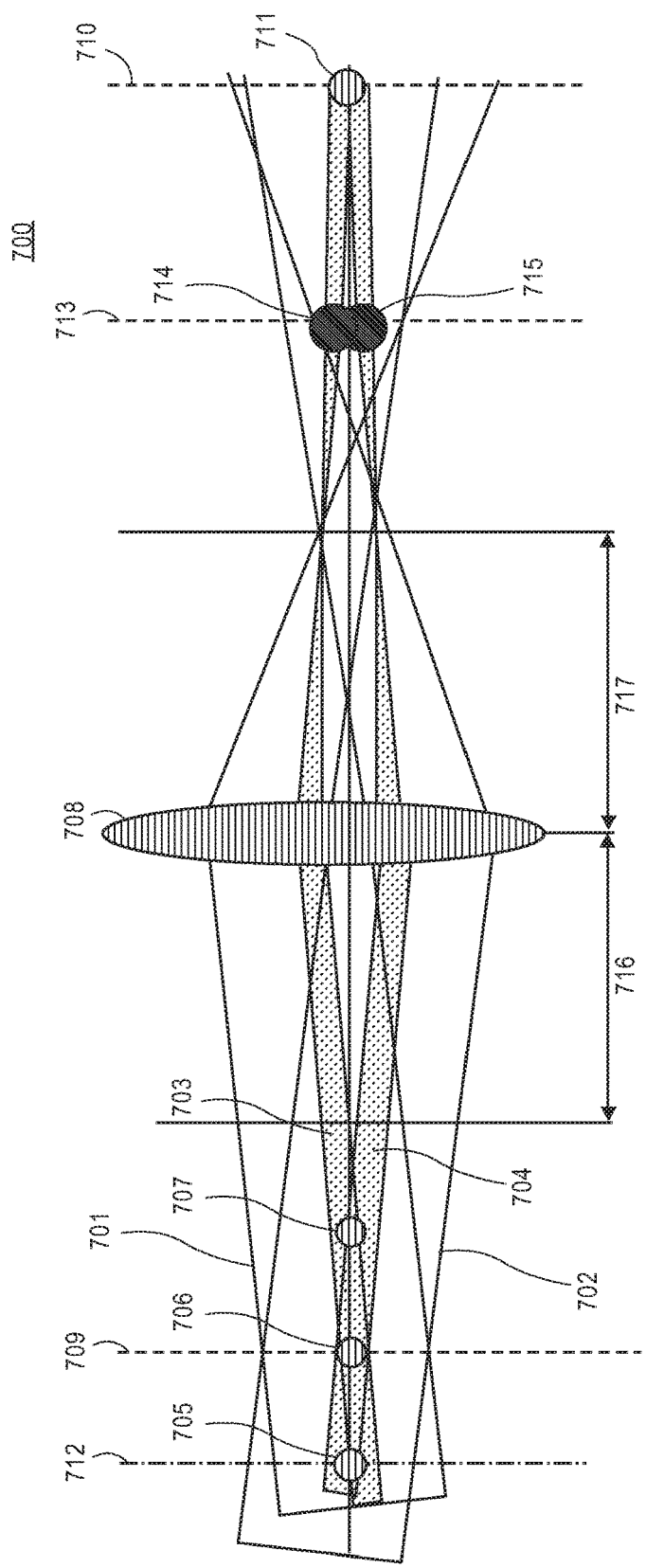
FIG. 7 is a schematic illustrating one embodiment of a multi-beam imaging system.

FIG. 7 is a schematic 700 illustrating one embodiment of a multi-beam imaging system. As shown in FIG. 7, intersecting illuminating light beams 701 and 702 propagate through a lens 708. Lens 708 has a focal distance 716 and a focal distance 717. Particles 705, 706, and 707 pass the measurement volume formed by overlapping illuminating light beams 701 and 702. Illuminating light beams forming the shadows of the particles, such as shadows 703 and 704, are admitted into the lens 708 and the digital camera—e.g., CMOS, CCD array, or other digital camera.

As shown in FIG. 7, particles 705 and 706 pass through the measurement volume at planes 712 and 709 respectively. Plane 709 is a focal plane of the lens 708. Particle 706 at the focal plane of the lens 708 produces a single focused shadow image 711 on an image plane 710 irrespective of the beam intersection angle or whether all beams are perfectly overlapped. Particle 705 is away from the focal plane of the lens. Particle 705 produces individual shadows, such as an individual shadow 714 and an individual shadow 715 on an image plane 713 that separate at a rate based on the illuminating beam intersection angle, as described above.

Figure 8:
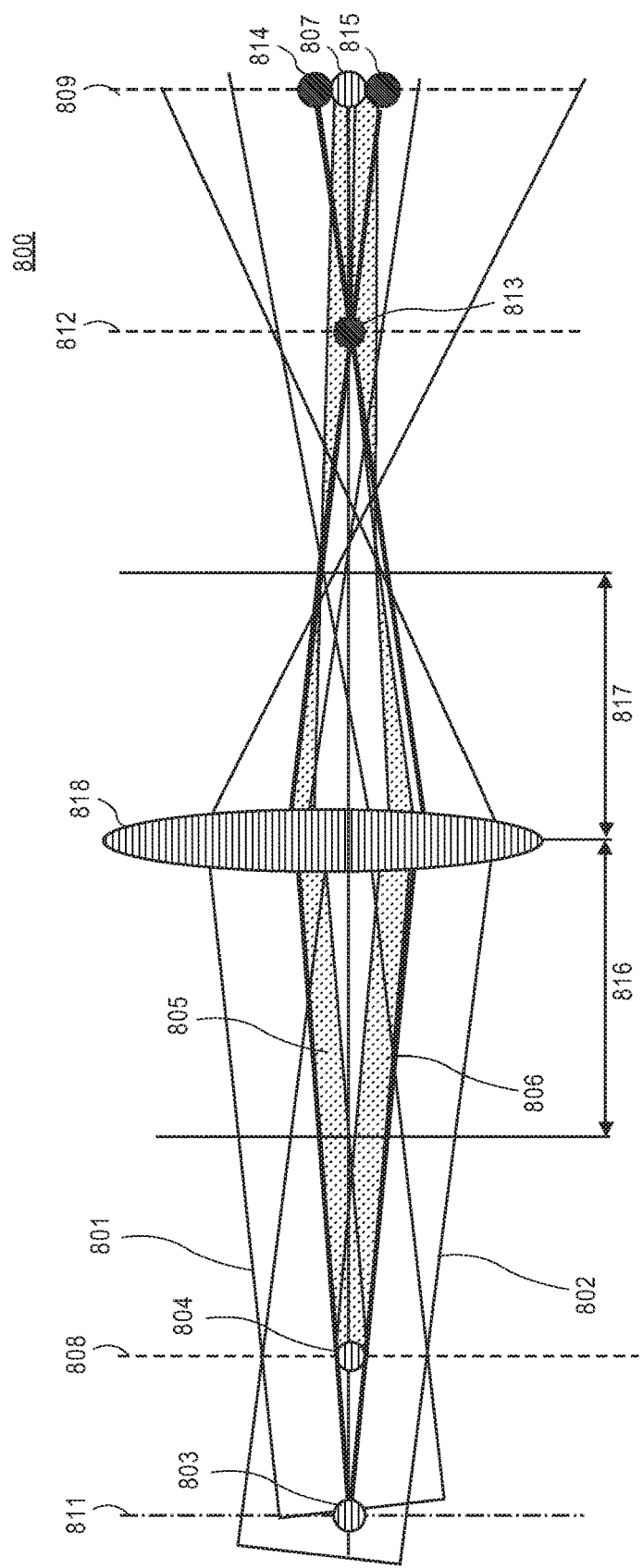
FIG. 8 is a schematic illustrating another embodiment of a multi-beam imaging system.

FIG. 8 is a schematic 800 illustrating another embodiment of a multi-beam imaging system. As shown in FIG. 8, intersecting illuminating light beams 801 and 802 propagate through a lens 818. Lens 818 has a focal distance 816 and a focal distance 817. Particles 803 and 804 pass the measurement volume formed by overlapping illuminating light beams 801 and 802 at planes 811 and 808 respectively. Illuminating light beams forming the shadows of the particles—such as shadows 805 and 806—are admitted into the lens 818 and the digital camera—e.g., CMOS, CCD array, or other digital camera.

Initially, plane 808 is a focal plane of the lens 818. Particle 804 at the focal plane of the lens 818 produces a single focused shadow image 807 on an image plane 809. Particles away from the focal plane, such as particle 803 produce two out of focus shadow images at the image plane, as described with respect to FIG. 7. After the camera is re-focused to plane 811, the individual shadows of particle 803 collapse onto a single shadow 813 at an image plane 812 whereas the shadow at image plane 809 will separate into an individual shadow 814 and an individual shadow 815.

Figure 9:
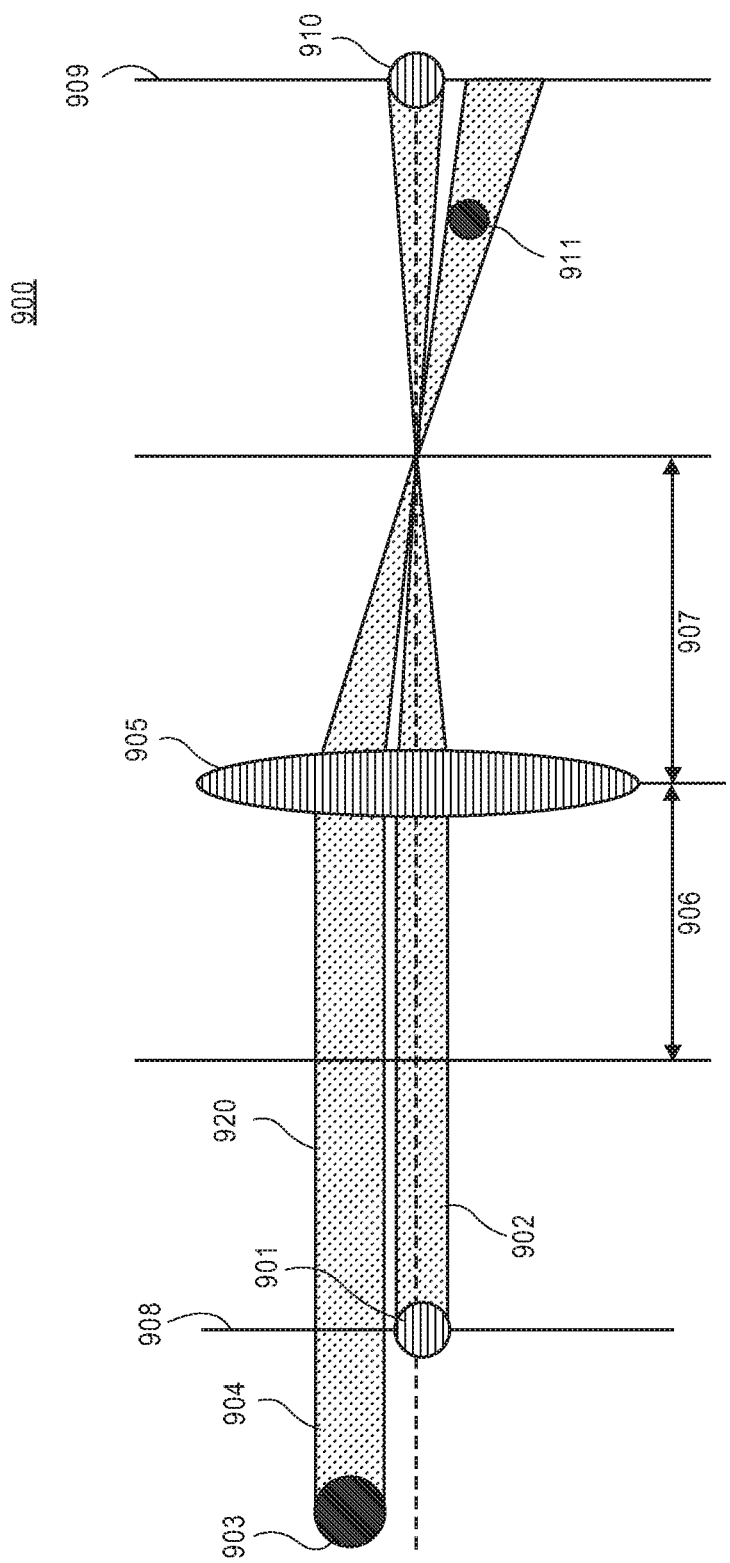
FIG. 9 is a schematic illustrating an embodiment of a single beam collimated light imaging system.

FIG. 9 is a schematic 900 illustrating an embodiment of a single beam collimated light imaging system. As shown in FIG. 9, particles 901 and 903 pass through a collimated light beam 920 creating shadows 902 and 904 respectively. The collimated light beam comprising shadows 902 and 904 propagates through a lens 905 to a digital camera having an image plane 909. Lens 905 has a focal distance 906 and a focal distance 907. Particle 901 passing the beam at a focal plane 908 of the lens 905 produces a shadow 910 on an image plane 909. Using collimated beam illumination, the shadow image 911 of particle 904 outside of the focal plane blurs and at some point, the blur circle or circle of confusion reach an unacceptable level. The depth of field and the circle of confusion are generally set by the requirements of the imaging system. The depth of field problem, however, is one of the most serious sources of measurement error when using imaging systems to measure particle size distributions. Generally, the depth of field refers to a range over which an optical instrument produces a sharp image of an object. Particles detected outside of the depth of field of the receiver optics cause a significant increase in the measurement error because the sizes of the unfocused particle images appear to be different from the true values.

Figure 10:
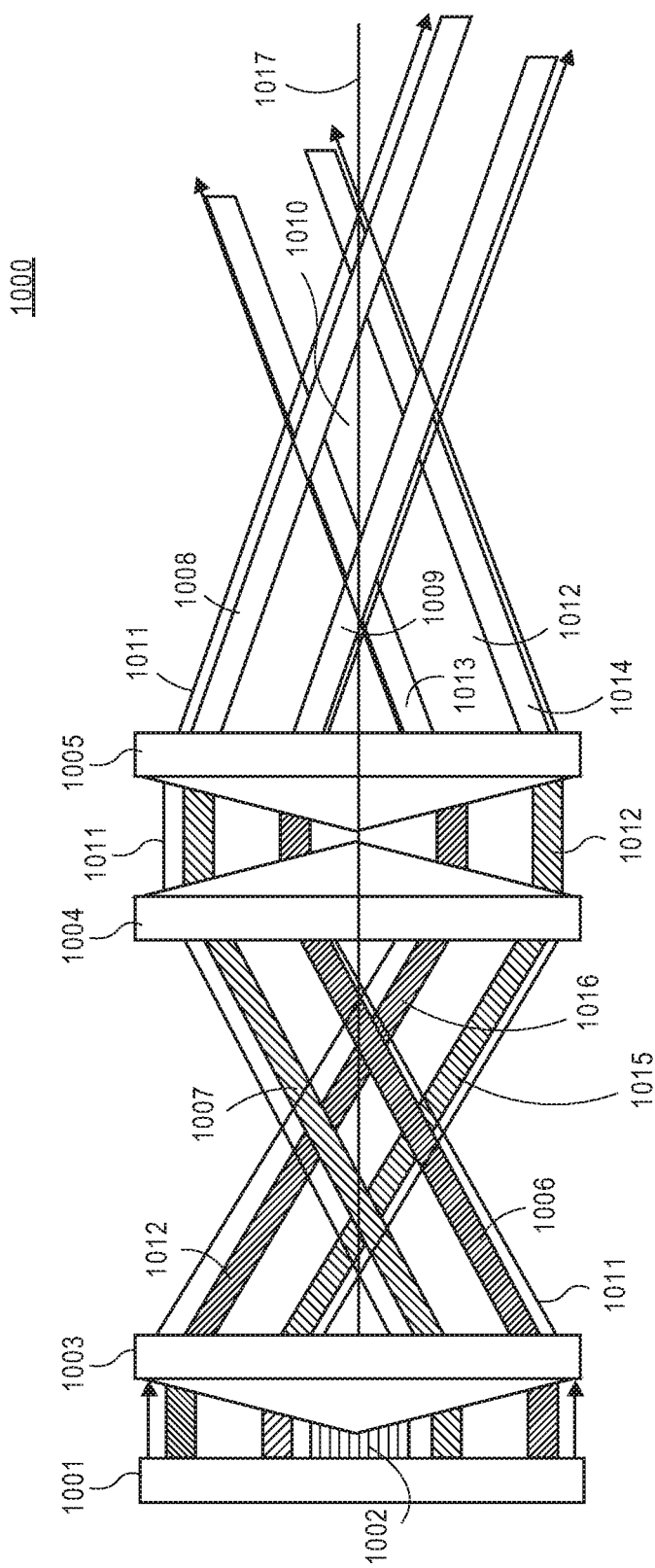
FIG. 10 is a view one embodiment of a system to image particles using one or more axicons.

FIG. 10 is a view one embodiment of a system 1000 to image particles using one or more axicons. A light beam 1001 having an uniform illumination passes through an axicon 1003, an axicon 1004 and an axicon 1005 to form a convergent light comprising a portion 1012 and a portion 1011 that converge at a predetermined angle to form a measurement volume 1010. The measurement volume 1010 is a region where the converging portions 1012 and 1011 of the beam 1001 overlap. As shown in FIG. 10, converging portion 1011 comprises an outer portion 1006 and an inner portion 1007 propagating from axicon 1003 through axicon 1004 to axicon 1005. Converging portion 1012 comprises an inner portion 1015 and an outer portion 1016 propagating from axicon 1003 through axicon 1004 to axicon 1005. Portions 1006 and 1016 are large radii portions, and portions 1007 and 1015 are small radii portions. The light intensity of the portions 1006 and 1016 is higher than that of portions 1007 and 1015. The light intensity at the intersection of the converging portions 1012 and 1011 between axicons 1003 and 1004 is non-uniform.

Figure 11:
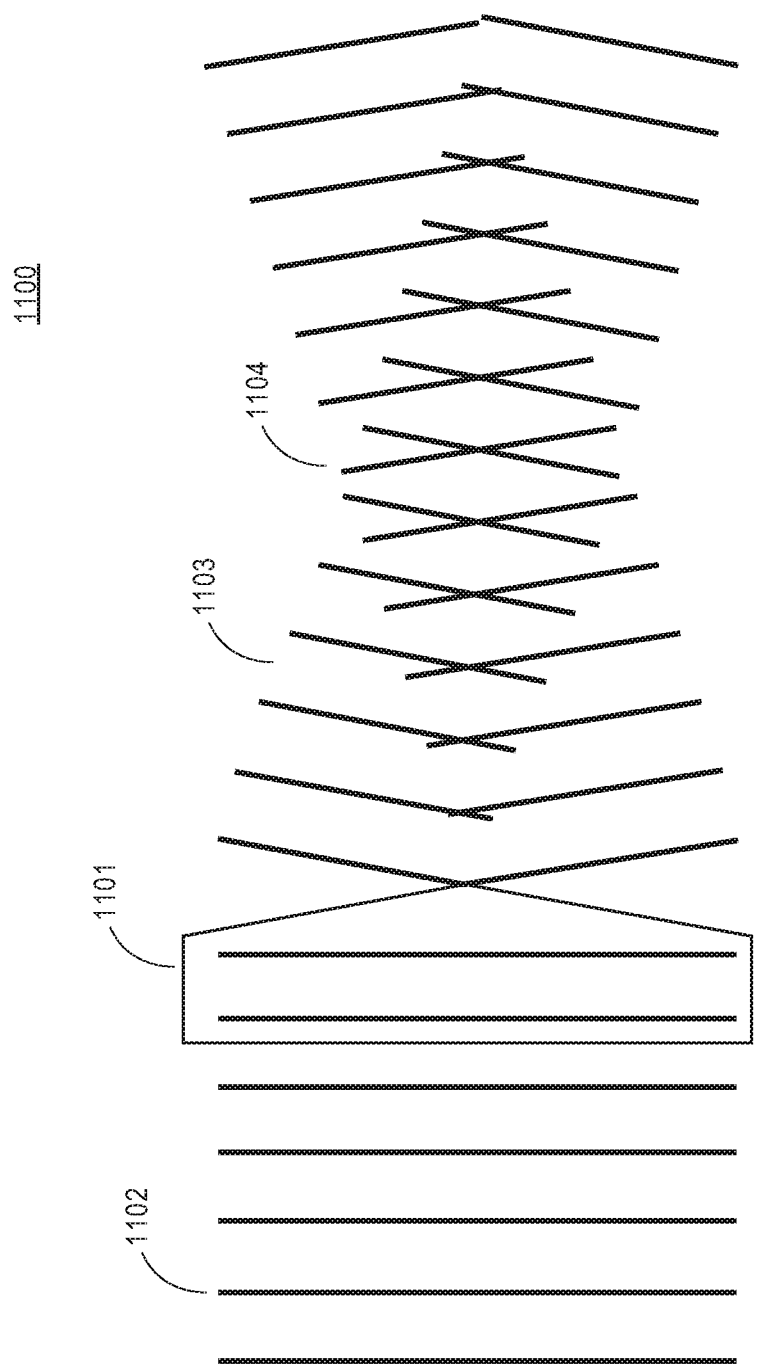
FIG. 11 is a schematic illustrating one embodiment of propagating a light through a single axicon.

FIG. 11 is a schematic 1100 illustrating one embodiment of propagating a light through a single axicon. A light having an uniform illumination 1102 passes through an axicon 1101 to form a convergent light comprising a portion 1103 and a portion 1104. At the intersection of the portions 1104 and 1103 the light has a nonuniform illumination. This is an undesirable consequence of the relative areas as a function of radii for the axicon. Larger radii collect more light and produce a higher intensity at the outer radii in the vicinity of the beam intersection. A low intensity will be produced near the center or axis of the beams due to the smaller radii associated with the light transmission.

Referring back to FIG. 10, by introducing a pair of axicons 1004 and 1005, the nonuniform light intensity at the intersection of the converging portions 1012 and 1011 between axicons 1003 and 1004 is inverted to produce an uniform illumination at the measurement volume 1010 similar to the uniform illumination of beam 1001. This provides an advantage of having a convergent illuminating beam that is not focusing and has an uniform radial intensity similar to the original incident illumination. As shown in FIG. 10, after passing through axicon 105, respective outer portions 1008 and 1014 and inner portions 1009 and 1013 of converging portions 1012 and 1011 have similar intensity.

As shown in FIG. 10, a block 1002 is placed between the illuminating light beam 1001 and axicon 1003. Block 1002 blocks a portion of the beam 1001 from passing through axicon 1003 to adjust the measurement volume 1010. For one embodiment, the measurement volume 1010 is adjusted by adjusting the size of the block 1002, the position of the block 1002 along the axicon 1003, or both. For an embodiment, the illumination produced by the axicons is a hollow cone illumination which is essentially a continuum of illumination angles. The hollow cone illumination is used to optimize the effect of eliminating shadows of particles and other structures outside of the image plane. For an embodiment the beam stop block forms a co-annular beam which can be advantageous in illuminating a dense particle field.

Figure 12:
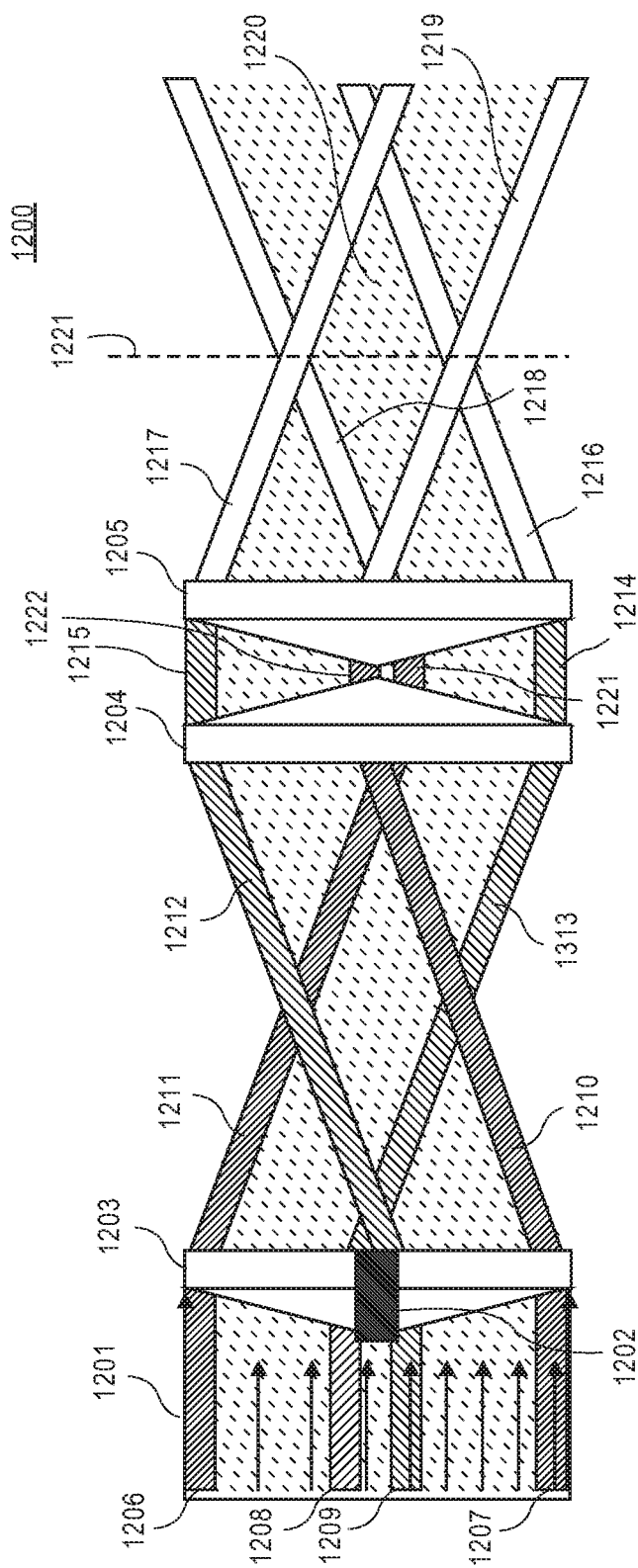
FIG. 12 is a view one embodiment of a system to image particles using one or more axicons.

FIG. 12 is a view one embodiment of a system 1200 to image particles using one or more axicons. An incident light beam 1201 has an uniform illumination. Portions 1206, 1208, 1209, and 1207 of the incident light beam 1201 have similar intensity. The incident light beam 1201 passes through an axicon 1203, an axicon 1204 and an axicon 1205 to form a convergent light comprising converging portions 1210, 1211, 1212, and 1213 that converge at a predetermined angle to form a measurement volume 1220. The light intensity of the portions 1211 and 1210 is higher than the light intensity of the portions 1212 and 1213, as described above with respect to FIGS. 10 and 11. The light intensity of the portions 1215 and 1214 is higher than the light intensity of the portions 1221 and 1222. After passing the axicon 1205 the nonuniform intensity is perfectly inverted to produce an uniform illumination in measurement volume 1220 at a plane 1221. The light intensity at measurement volume 1220 at a plane 1221 is similar to the light intensity of incident beam 1201.

For an embodiment, the illumination produced by the axicons as shown in FIGS. 10 and 12 is a hollow cone illumination which is essentially a continuum of illumination angles. The hollow cone illumination is used to optimize the effect of eliminating shadows of particles and other structures outside of the image plane.

Figure 13:
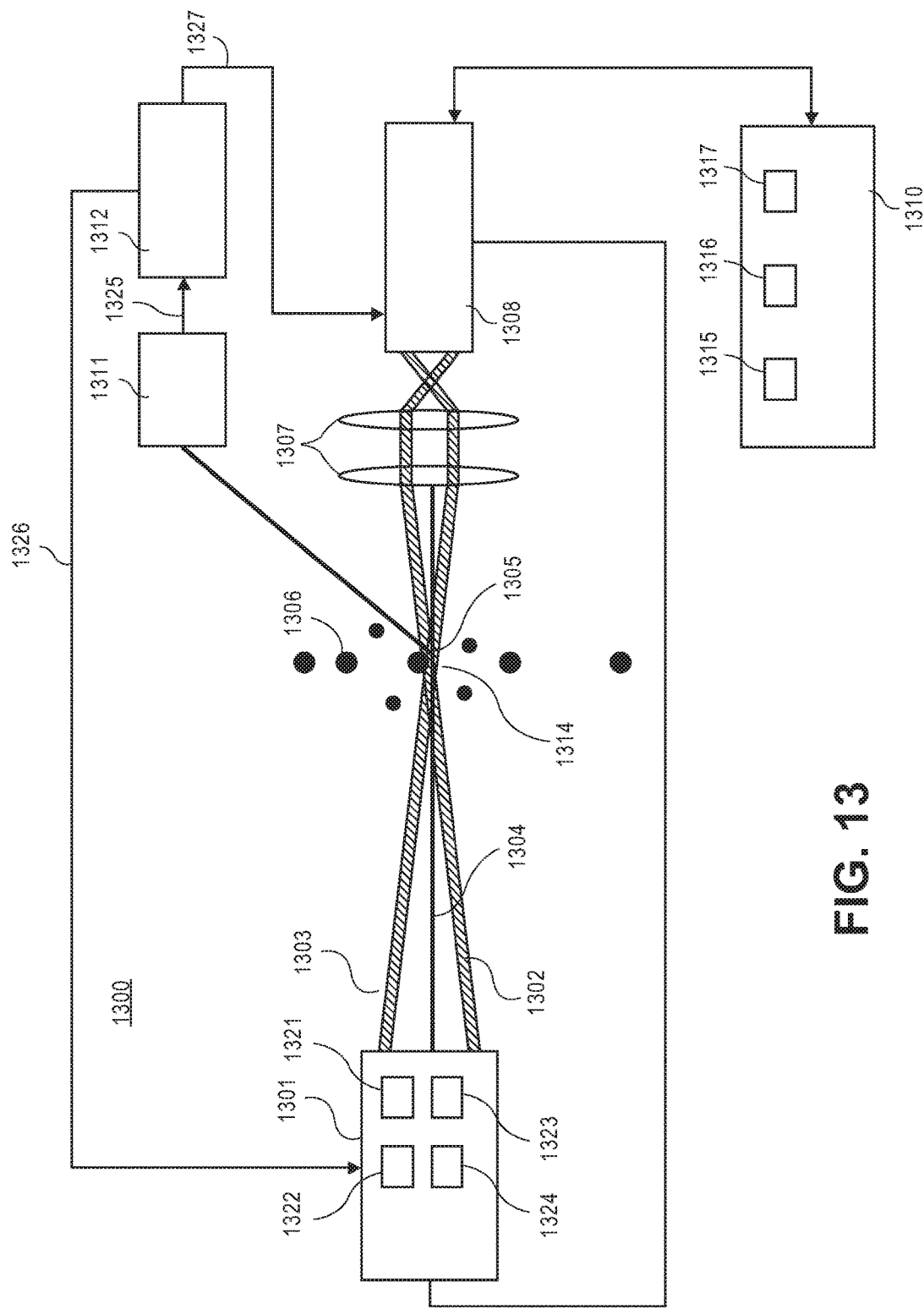
FIG. 13 is a view showing another embodiment of a system to image particles.

FIG. 13 is a view showing another embodiment of a system 1300 to image particles. System 1300 comprises a transmitter system 1301. Transmitter system 1301 comprises one or more light sources—e.g., a light source 1321 and a light source 1322—generating a plurality of illuminating light beams, such as a light beam 1302 and 1303 and a light source 1323 to generate a triggering light beam 1304. The transmitter system 1301 comprises a synchronization module 1324 to synchronize the illuminating light beams with a digital camera system 1308. The illuminating light beams are configured to propagate on multiple optical paths through a particle field comprising particles—e.g., particles 1305 and 1306. The illuminating light beams are configured to converge to form a measurement volume 1304 at a focal plane of the imaging system. The illuminating light beams of FIG. 13 are represented by the illuminating light beams of FIGS. 1 and 2. For an embodiment, the illuminating light sources of the transmitter system 301 comprise lasers, light emitting diodes ("LEDs"), or both, as described above with respect to FIGS. 1 and 2. For an embodiment, the plurality of illuminating light beams are generated by a single light source using axicons, as described with respect to FIGS. 10-12.

For an embodiment, the triggering light beam 1304 generated by the triggering light source propagates through a center of the measurement volume 1314. For an embodiment, the triggering light source comprises a laser, an LED, or both.

A receiver system comprises an imaging optics—e.g., one or more lenses 1307—and a digital camera system 1308 comprising one or more digital cameras to provide a shadow image of the particle passing through the measurement volume at a focal plane, as described above. For one embodiment, the wavelength of the triggering beam is different from the wavelength of the illuminating light beams. When a particle passes through the measurement volume, the triggering light beam 1304 is deflected from the particle onto photodetector system 1311 that outputs a trigger signal 1325 indicating the presence of the particle in the measurement volume 1314 to a a logic circuitry 1312 to drive one or more laser sources. Logic circuitry 1312 outputs a trigger signal 1326 to drive one or more light sources of the transmitter system 1301 to generate converging illuminating light beams. Logic circuitry 1312 outputs a trigger signal 1325 to trigger digital camera system 1308. For one embodiment, multiple diode lasers are used to simultaneously illuminate a particle field from multiple directions. A trigger laser and photodetector are used to detect the presence of particles in the measurement volume. This information is used to pulse the multiple illumination beams. The laser beams are combined by a receiver lens which creates a frozen shadow (e.g., bright-field image) of the particles on the CMOS sensor. The use of multi-angle illumination significantly reduces measurement errors due to depth-of-field variations that are a problem for conventional instruments.

The imaging system can optionally comprise one or more beam splitters (not shown) to split the illuminating light beams onto multiple digital cameras, as described above with respect to FIG. 3. An image acquisition and processing system 1310 is coupled to the digital camera system 1310. Processing system 320 comprises a processor 1315, a memory 1316, and a display 1317 to perform methods to image shadows of the particles passing through the measurement volume, as described herein. For an embodiment, processor 1315 is configured to perform particle analysis that involves identifying particles that are in-focus, calculating various shape parameters, and classifying particles. For an embodiment, processor 1315 is configured to differentiate between liquid drops and ice crystals.

Figure 14:
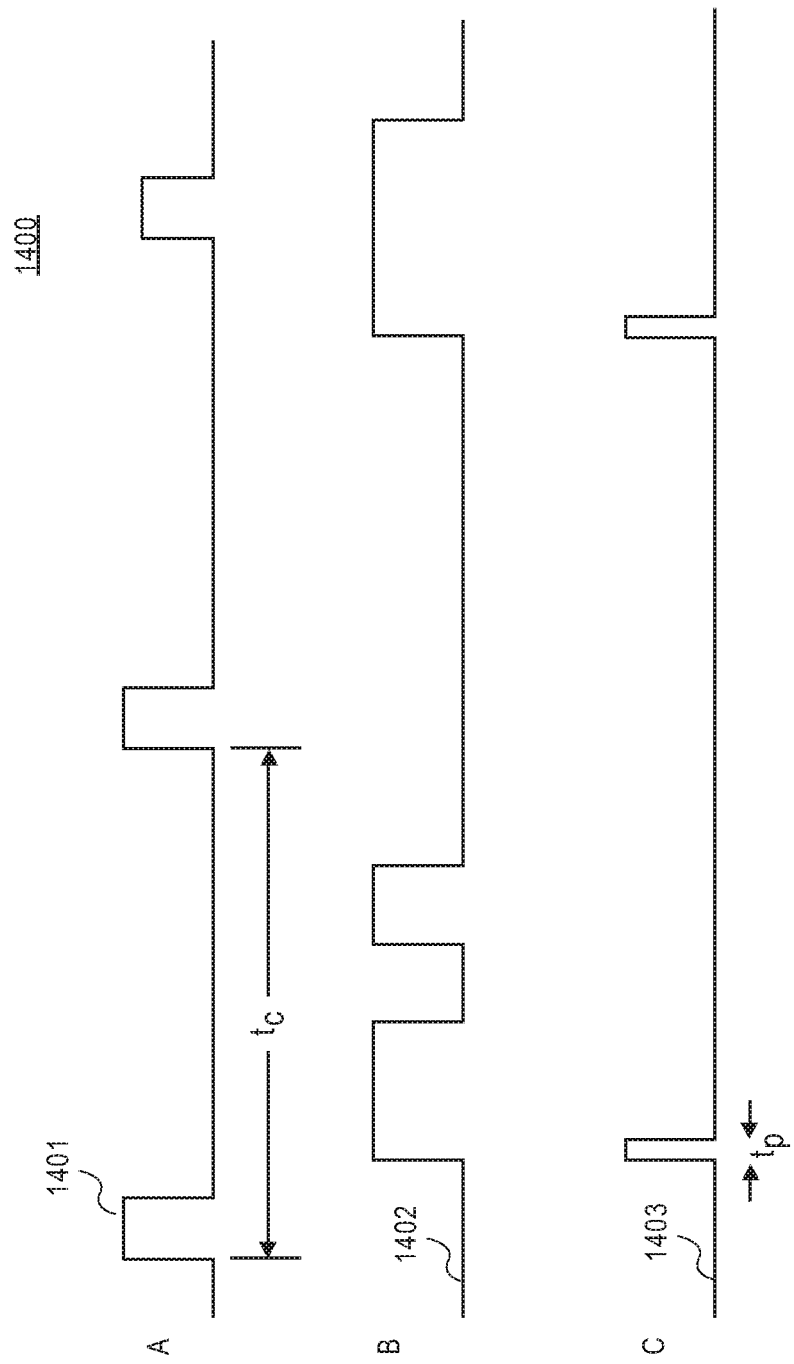
FIG. 14 is a view illustrating one embodiment of a digital camera frame rate signal, a trigger signal indicating detection of the particle and a trigger signal sent to the transmitter to generate converging illuminating light beams.

FIG. 14 is a view 1400 illustrating one embodiment of a digital camera frame rate signal 1401, a trigger signal 1402 indicating detection of the particle and a trigger signal 1403 sent to the transmitter to generate converging illuminating light beams. For an embodiment, trigger signal 1402 represents trigger signal 1325. For an embodiment, trigger signal 1403 represents trigger signal 1326. As shown in FIG. 14, the signal 1403 is a pulsed signal having the width tp. As shown in FIG. 14, only one trigger signal 1403 is issued during a camera frame time tc.

Figure 15:
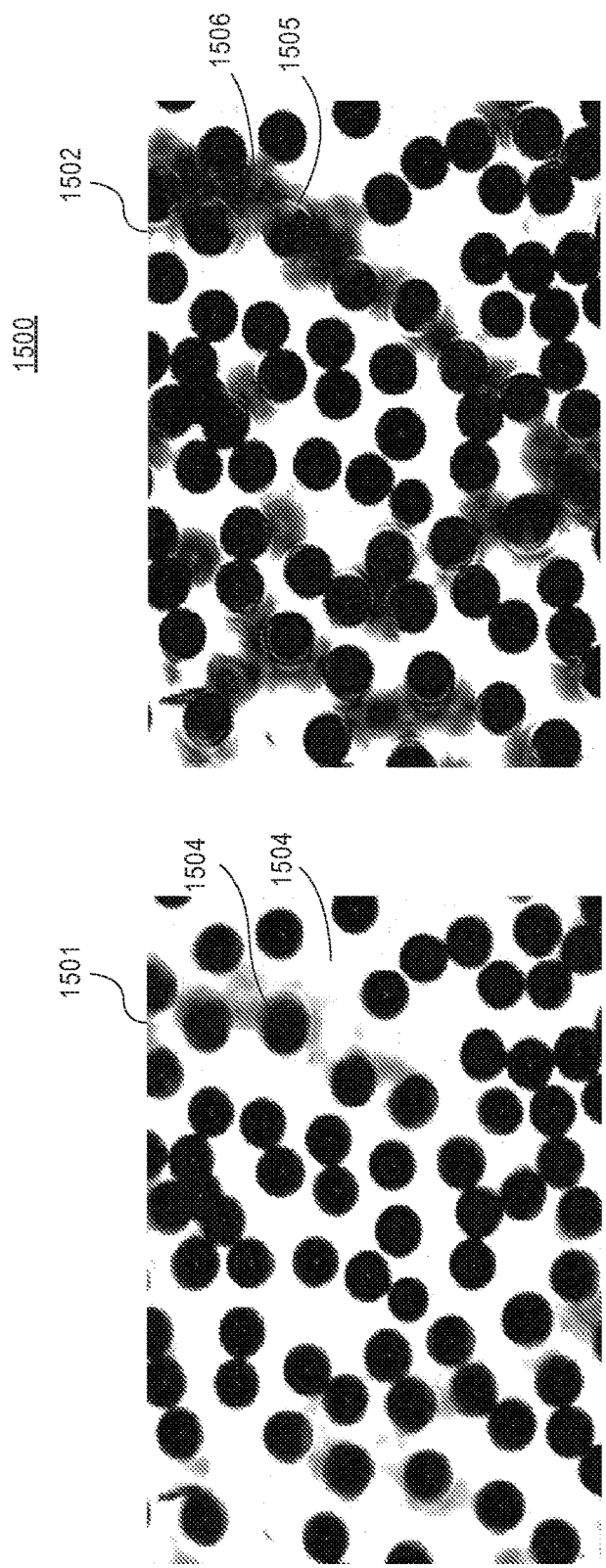
FIG. 15 is a view illustrating an exemplary image taken using illumination converging at a measurement volume in a dense region of the particle field and an exemplary image taken with collimated illumination in the same region of the particle field.

FIG. 15 is a view 1500 illustrating an exemplary image 1501 taken using illumination converging at a measurement volume in a dense region of the particle field and an exemplary image 1502 taken with collimated illumination in the same region of the particle field. Image 1501 displays full shadow images of the particles passing through a portion of the measurement volume at a focal plane of a digital camera, such as a full shadow image 1503 against a background 1504. Background 1504 is substantially clean even though the converging light beams pass through a relatively dense particle field adjacent to the focal plane. Image 1501 shows that shadow images of the out of focus particles are eliminated from background using the converging illumination. Image 1502 shows the same particle field imaged with a single collimated beam. Full shadow images of the particles passing through a portion of the measurement volume at a focal plane of a digital camera, such as a full shadow image 1505 are obscured by background shadow images of the out of focus particles, such as a background shadow image 1506. As shown in image 1502, the out of focus dense particle clusters produce pronounced obscuration that creates problems for the image processing.

Figure 16A:
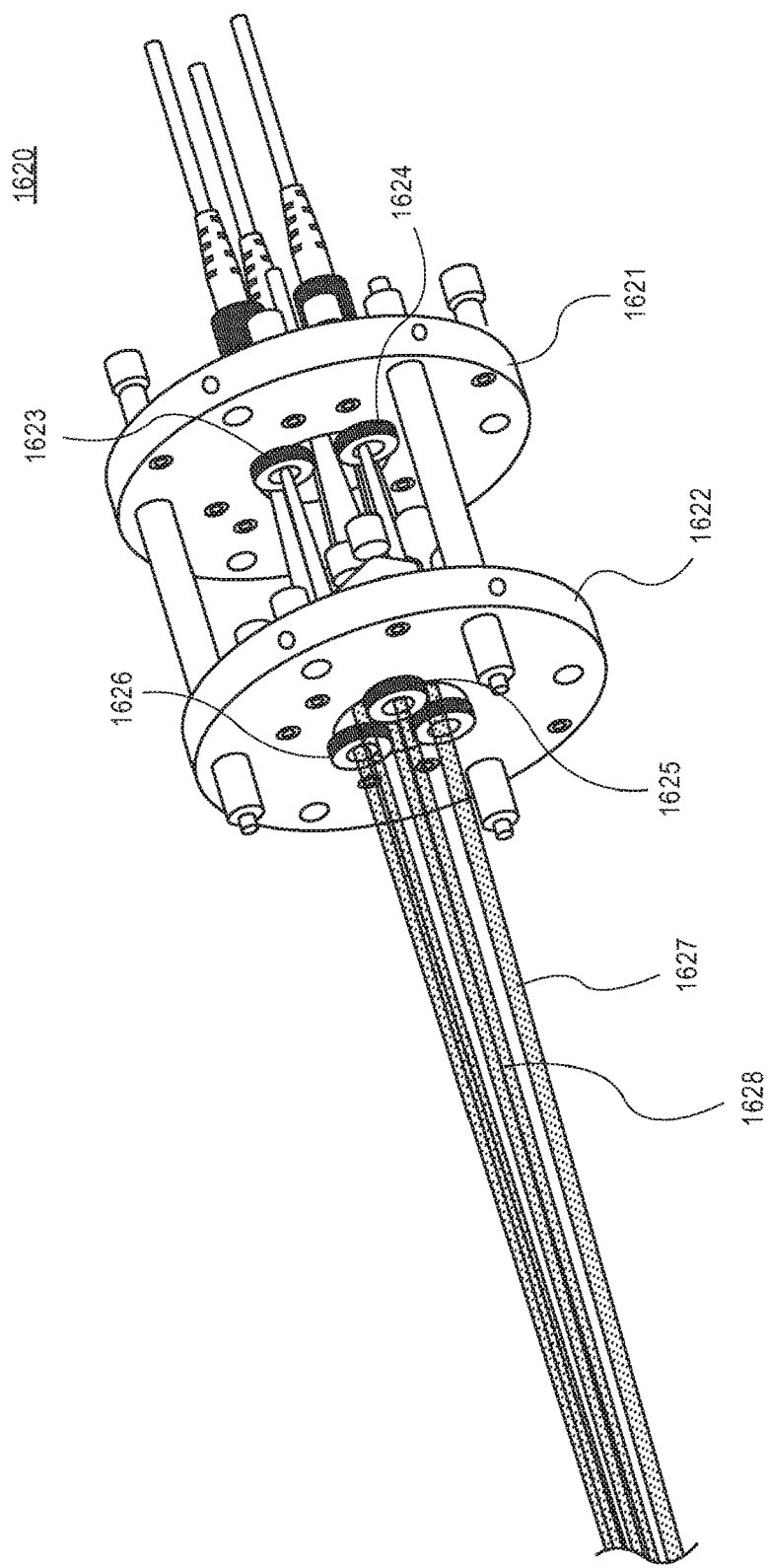
FIG. 16A illustrates one embodiment of a system to image particles.

FIG. 16A illustrates one embodiment of a system to image particles. A system 1620 comprises one or more mounting fixtures, such as a mounting fixture 1621 and a mounting fixture 1622. Mounting fixture 1621 holds a portion of a transmitter sub-system comprising a plurality of laser sources, such as a laser source 1623 and a laser source 1624. Mounting fixture 1622 holds a portion of the transmitter sub-system comprising a plurality of laser sources, such as a laser source 1625 and a laser source 1626. Each of the laser sources comprises a focusing lens coupled to an output of the laser diode to form an illuminating laser beam. A plurality of illuminating laser beams, such as an illuminating laser beam 1627 and an illuminating laser beam 1628 are generated from the laser sources to propagate on multiple optical paths through a particle field and to converge at a measurement volume. For an embodiment, system 1600 comprises a receiver module (not shown) comprising an imaging optics to provide a shadow image of a particle passing through the measurement volume at a focal plane of the first digital camera, as described above.

Figure 16B:
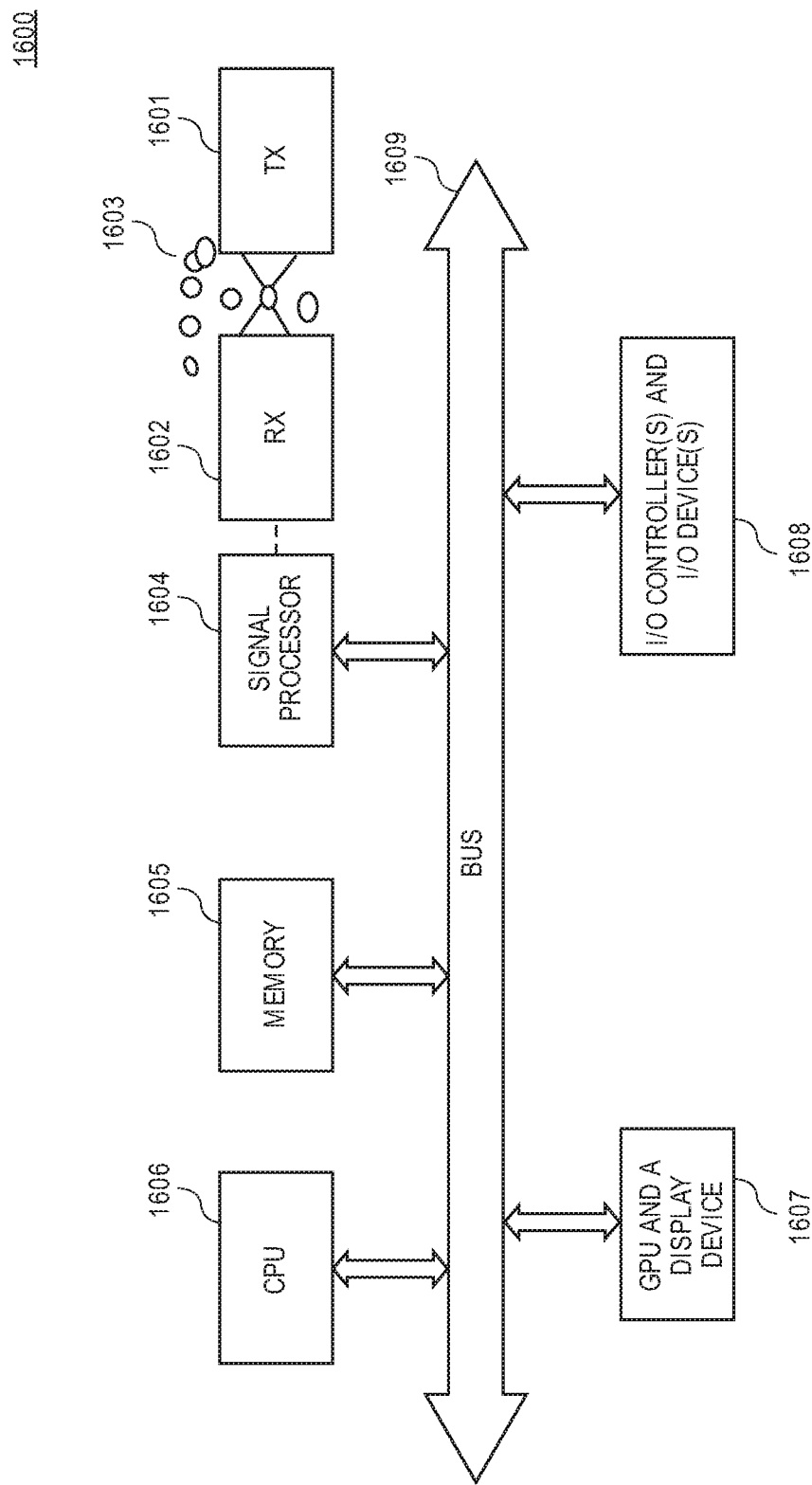
FIG. 16B illustrates one embodiment of a system to image particles.

FIG. 16B illustrates one embodiment of a system to image particles. As shown on FIG. 16B, system 1600 includes a transmitter 1605 to generate illuminating light beams converging to form a measurement volume to illuminate particles 1603, as described above. As shown in FIG. 16B, a receiver 1602 is coupled to receive the shadows of particles 1603, as described above. As shown in FIG. 16B, receiver 1606 is coupled to a signal processor 1604. As shown in FIG. 16B, a subsystem 1606 comprising a central processing unit ("CPU"), a subsystem 1607 comprising a graphics processing unit ("GPU"), that may be coupled with a display device, one or more subsystems 1608 comprising one or more I/O controllers coupled to one or more I/O devices, a memory 1605 (comprising a volatile RAM, a ROM and a non-volatile memory (e.g., flash memory or a hard drive), or any combination thereof), and a signal processor 1604 comprising a microcontroller are coupled to a bus 1609. At least one of a subsystem 1606 and a signal processor 1604 are configured to perform methods as described above. Memory 1605 may be used to store data that when accessed by the data processing system, cause the data processing system to perform one or more methods to image particles, as described above.

In the foregoing specification, the invention has been described with reference to specific exemplary embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method to image particles, comprising:
   generating a plurality of illuminating light beams propagating on multiple optical paths through a particle field, wherein the plurality of illuminating light beams are laser beams that converge at a measurement volume; and
   imaging a shadow image of a particle passing through a portion of the measurement volume at a focal plane of a first digital camera using the plurality of converging laser beams, wherein the shadow image is a superposition of individual shadow images produced by each of the converging laser beams, and wherein individual shadow images of other particles in the particle field outside the focal plane produced by each of the plurality of converging laser beams do not overlap and are separated from the shadow image by a distance so that the shadow image of the particle is not obscured by the other particles, wherein an intersection angle of the plurality of illuminating light beams is adjusted to remove shadow images of the particles outside the measurement volume.

2. The method of claim 1, wherein the plurality of illuminating light beams comprise multiple wavelengths.

3. The method of claim 1, further comprising
   adjusting a dynamical range of the particles using a plurality of digital cameras.

4. The method of claim 1, wherein at least one of the plurality of illuminating light beams is pulsed.

5. The method of claim 1, further comprising
   determining if the particle is in the measurement volume using a triggering laser beam that is configured to propagate through the measurement volume, wherein the triggering laser beam is scattered by the particle and detected by a photodetector system when the particle is in the measurement volume, and
   sending a trigger signal to one or more laser sources to generate the plurality of converging laser beams in response to the triggering laser beam that is detected by the photodetector system, to locate the shadow image of the particle in an image frame.

6. The method of claim 1, further comprising
detecting the shadow image;
evaluating at least one of a depth of field of the particle and a focus of the particle based on the shadow image; and
determining a particle information based on the evaluating.

7. The method of claim 1, further comprising
determining at least one of a size or a shape of the particle based on the shadow image.

8. The method of claim 1, further comprising
synchronizing the plurality of illuminating light beams with the first digital camera.

9. The method of claim 1, wherein the plurality of illuminating light beams are converged using one or more axicons.

10. The method of claim 1, further comprising
adjusting at least one of a quantity of the illuminating light beams, and a light beam wavelength to remove shadow images of the particles outside the measurement volume.

11. The method of claim 1, further comprising
determining a delay between the plurality of the illuminating laser light beams to obtain an information about the particle.

12. A non-transitory machine-readable medium comprising data that when accessed by a data processing system, cause the data processing system to perform a method to image particles comprising:
generating a plurality of illuminating light beams propagating on multiple optical paths through a particle field, wherein the plurality of illuminating light beams are laser beams converging at a measurement volume; and
imaging a shadow image of a particle present through a portion of the measurement volume at a focal plane of a first digital camera using the plurality of converging laser beams, wherein the shadow image is a superposition of individual shadow images produced by each of the converging laser beams, and wherein individual shadow images of other particles in the particle field outside the focal plane produced by each of the plurality of converging laser beams do not overlap and are separated from the shadow image by a distance so that the shadow image of the particle is not obscured by the other particles, wherein an intersection angle of the plurality of illuminating light beams is adjusted to remove shadow images of the particles outside the measurement volume.

13. The non-transitory machine-readable medium of claim 12, wherein the plurality of illuminating light beams comprise multiple wavelengths.

14. The non-transitory machine-readable medium of claim 12, further comprising instructions to cause the data processing system to perform operations comprising
adjusting a dynamical range of the particles using a plurality of digital cameras.

15. The non-transitory machine-readable medium of claim 12, wherein at least one of the plurality of illuminating light beams is pulsed.

16. The non-transitory machine-readable medium of claim 12, further comprising instructions to cause the data processing system to perform operations comprising
determining if the particle is in the measurement volume using a triggering laser beam that is configured to propagate through the measurement volume, wherein the triggering laser beam is scattered by the particle and detected by a photodetector system when the particle is in the measurement volume, and
sending a trigger signal to one or more laser sources to generate the plurality of converging laser beams in response to the triggering laser beam that is detected by the photodetector system, to locate the shadow image of the particle in an image frame.

17. The non-transitory machine-readable medium of claim 12, further comprising instructions to cause the data processing system to perform operations comprising
detecting the shadow image;
evaluating at least one of a depth of field of the particle and a focus of the particle based on the shadow image; and
determining a particle information based on the evaluating.

18. The non-transitory machine-readable medium of claim 12, further comprising instructions to cause the data processing system to perform operations comprising
determining at least one of a size or a shape of the particle based on the shadow image.

19. The non-transitory machine-readable medium of claim 12, further comprising instructions to cause the data processing system to perform operations comprising
synchronizing the plurality of illuminating light beams with the first digital camera.

20. The non-transitory machine-readable medium of claim 12, wherein the plurality of illuminating light beams are converged using one or more axicons.

21. The non-transitory machine-readable medium of claim 12, further comprising instructions to cause the data processing system to perform operations comprising
adjusting at least one of a quantity of the illuminating light beams, and a light beam wavelength to remove shadow images of the particles outside the measurement volume.

22. The non-transitory machine-readable medium of claim 12, further comprising instructions to cause the data processing system to perform operations comprising
determining a delay between the plurality of the illuminating laser light beams to obtain an information about the particle.

23. An apparatus to image particles, comprising:
a transmitter comprising one or more laser sources to generate a plurality of illuminating light beams propagating on multiple optical paths through a particle field, wherein the plurality of illuminating light beams are laser beams converging at a measurement volume;
a receiver coupled to the transmitter, the receiver comprising
a photodetector system;
an imaging optics; and
a first digital camera coupled to the imaging optics to provide a shadow image of a particle passing through the measurement volume at a focal plane of the first digital camera using the plurality of converging laser beams, wherein the shadow image is a superposition of individual shadow images produced by each of the converging laser beams, and wherein individual shadow images of other particles in the particle field outside the focal plane produced by each of the plurality of converging laser beams do not overlap and are separated from the shadow image by a distance so that the shadow image of the particle is not obscured by the other particles in the particle field, wherein an intersection angle of the plurality of illuminating light beams is adjusted to remove shadow images of the particles outside the measurement volume; and a processor coupled to least one of the transmitter and the receiver.

24. The apparatus of claim 23, wherein the plurality of illuminating light beams comprise multiple wavelengths.

25. The apparatus of claim 23, further comprising one or more second digital cameras coupled to the first digital camera to adjust a dynamic range of the particles.

26. The apparatus of claim 23, wherein at least one of the plurality of illuminating light beams is pulsed.

27. The apparatus of claim 23, wherein the transmitter comprises a trigger light source to send a triggering laser beam that is configured to propagate through the measurement volume, wherein the triggering laser beam is scattered by the particle and detected by the photodetector system when the particle is in the measurement volume, wherein the photodetector system is configured send a trigger signal to the one or more laser sources to generate the plurality of converging laser beams in response to detecting the triggering laser beam, to locate the shadow image of the particle in an image frame.

28. The apparatus of claim 23, wherein the processor is configured to detect the shadow image, to evaluate at least one of a depth of field of the particle and a focus of the particle based on the shadow image, to determine a particle information based on the evaluation.

29. The apparatus of claim 23, wherein the processor is configured to determine at least one of a size or a shape of the particle based on the shadow image.

30. The apparatus of claim 23, further comprising a synchronization module to synchronize the plurality of illuminating light beams with the first digital camera.

31. The apparatus of claim 23, further comprising one or more axicons to converge the plurality of illuminating light beams.

32. The apparatus of claim 23, wherein at least one of a quantity of the illuminating light beams, and a light beam wavelength is adjusted to remove shadow images of the particles outside the measurement volume.

33. The apparatus of claim 23, wherein a delay between the plurality of the illuminating laser light beams is determined to obtain an information about the particle.

\* \* \* \* \*